United States Patent
Fang et al.

(10) Patent No.: US 7,632,509 B2
(45) Date of Patent: *Dec. 15, 2009

(54) METHODS TO EXPRESS RECOMBINANT PROTEINS FROM LENTIVIRAL VECTORS

(75) Inventors: Jianmin Fang, Palo Alto, CA (US); Karin Jooss, Bellevue, WA (US); Andrew Simmons, San Mateo, CA (US); Debbie Farson, San Francisco, CA (US); Jing Jing Qian, Foster City, CA (US)

(73) Assignee: BioSante Pharmaceuticals, Inc., Lincolnshire, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/488,568

(22) Filed: Jul. 18, 2006

(65) Prior Publication Data

US 2007/0059820 A1    Mar. 15, 2007

Related U.S. Application Data

(60) Provisional application No. 60/700,298, filed on Jul. 19, 2005.

(51) Int. Cl.
*A61K 39/21*    (2006.01)
*A61K 39/38*    (2006.01)
*A61K 39/295*   (2006.01)
*C12N 7/00*     (2006.01)
*C12N 7/02*     (2006.01)
*C12N 15/00*    (2006.01)
*C07K 16/00*    (2006.01)
*A61K 39/395*   (2006.01)
*A61K 39/275*   (2006.01)

(52) U.S. Cl. ............... 424/207.1; 424/199.1; 424/184.1; 424/202.1; 424/130.1; 435/320.1; 435/235.1; 435/239; 530/387.1

(58) Field of Classification Search ................. None
See application file for complete search history.

(56) References Cited

U.S. PATENT DOCUMENTS

| | | | |
|---|---|---|---|
| 5,310,903 A | 5/1994 | Goulet et al. | |
| 5,362,718 A | 11/1994 | Skotnicki et al. | |
| 5,436,146 A | 7/1995 | Shenk et al. | |
| 5,525,610 A | 6/1996 | Caufield et al. | |
| 5,573,500 A | 11/1996 | Katsunuma | |
| 5,686,279 A | 11/1997 | Finer et al. | |
| 5,846,767 A | 12/1998 | Halpin et al. | |
| 6,015,709 A | 1/2000 | Natesan | |
| 6,040,183 A | 3/2000 | Ferrari et al. | |
| 6,093,570 A | 7/2000 | Ferrari et al. | |
| 6,117,680 A | 9/2000 | Natesan et al. | |
| 6,133,456 A | 10/2000 | Holt et al. | |
| 6,150,527 A | 11/2000 | Holt et al. | |
| 6,171,586 B1 * | 1/2001 | Lam et al. | 424/130.1 |
| 6,187,757 B1 | 2/2001 | Clackson et al. | |
| 6,261,567 B1 * | 7/2001 | Hart et al. | 424/199.1 |
| 6,306,649 B1 | 10/2001 | Gilman et al. | |
| 6,331,415 B1 | 12/2001 | Cabilly et al. | |
| 6,479,653 B1 | 11/2002 | Natesan et al. | |
| 6,506,379 B1 | 1/2003 | Clackson et al. | |
| 6,548,286 B1 | 4/2003 | Samulski et al. | |
| 6,602,503 B1 | 8/2003 | Lobb et al. | |
| 6,623,940 B1 | 9/2003 | Ledbetter et al. | |
| 6,632,800 B1 * | 10/2003 | Russell et al. | 514/44 |
| 6,649,595 B2 | 11/2003 | Clackson et al. | |
| 6,692,736 B2 | 2/2004 | Yu et al. | |
| 6,933,362 B1 | 8/2005 | Belfort | |
| 7,001,596 B1 | 2/2006 | Johnson et al. | |
| 7,485,291 B2 | 2/2009 | Fang et al. | |
| 7,498,024 B2 | 3/2009 | Fang et al. | |
| 2002/0168339 A1 | 11/2002 | Piechaczyk et al. | |
| 2003/0068307 A1 | 4/2003 | Yu | |
| 2003/0099932 A1 | 5/2003 | Lorens | |
| 2004/0086485 A1 | 5/2004 | Cordova | |
| 2004/0131591 A1 | 7/2004 | Kingsman | |
| 2004/0209830 A1 | 10/2004 | Russell | |
| 2004/0235011 A1 | 11/2004 | Cooper | |
| 2004/0235173 A1 | 11/2004 | Bleck et al. | |
| 2004/0235955 A1 | 12/2004 | Fang et al. | |
| 2004/0265955 A1 * | 12/2004 | Fang et al. | 435/69.1 |

(Continued)

FOREIGN PATENT DOCUMENTS

| | | | |
|---|---|---|---|
| WO | WO 92/08793 | * | 5/1992 |
| WO | WO 97/28272 | | 8/1997 |
| WO | WO 2004/113493 | | 12/2004 |
| WO | WO 2007/126805 | | 11/2007 |

OTHER PUBLICATIONS

Lamikama et al., In vivo evaluation of an EIAV vector for the systemic genetic delivery of therapeutic antibodies, 2005, Gene Therapy, vol. 12, pp. 988-998.*

(Continued)

*Primary Examiner*—Gary B Nickol
*Assistant Examiner*—Benjamin P Blumel
(74) *Attorney, Agent, or Firm*—Ropes & Gray LLP; James F. Haley, Jr.; Teresa A. Chen

(57) ABSTRACT

Lentivector constructs for expression of recombinant proteins, polypeptides or fragments thereof and methods of making the same are described. The lentivectors typically have a self-processing cleavage sequence between a first and second protein or polypeptide coding sequence allowing for expression of a functional protein or polypeptide under operative control of a single promoter and may further include an additional proteolytic cleavage sequence which provides a means to remove the self-processing cleavage sequence from the expressed protein or polypeptide. The vector constructs find utility in methods relating to enhanced production of biologically active proteins, such as immunoglobulins or fragments thereof in vitro and in vivo.

16 Claims, 10 Drawing Sheets

U.S. PATENT DOCUMENTS

| | | |
|---|---|---|
| 2005/0003482 A1 | 1/2005 | Fang et al. |
| 2005/0042721 A1 | 2/2005 | Fang et al. |
| 2005/0060762 A1 | 3/2005 | Bleck |
| 2005/0095705 A1 | 5/2005 | Kadan et al. |
| 2006/0034805 A1* | 2/2006 | Fang et al. ............... 424/93.2 |
| 2006/0228336 A1* | 10/2006 | Ko ........................... 424/93.2 |
| 2006/0292682 A1 | 12/2006 | Hawkins et al. |
| 2007/0059820 A1 | 3/2007 | Fang et al. |
| 2007/0065912 A1 | 3/2007 | Carson et al. |
| 2007/0275915 A1 | 11/2007 | Hallenbeck et al. |
| 2007/0292922 A1 | 12/2007 | Fang et al. |
| 2008/0280356 A1 | 11/2008 | Fang et al. |

OTHER PUBLICATIONS

O'Rourke et al., Comparison of Gene Transfer Efficiencies and Gene Expression Levels Achieved with Equine Infectious Anemia Virus- and Human Immunodeficiency Virus Type 1-Derived Lentivirus Vectors, 2002, Journal of Virology, vol. 76, No. 3, pp. 1510-1515.*

Chazenbalk et al., Evidence for negative cooperativity among human thyrotropin receptors overexpressed in mammalian cells, 1996, Endocrinology, vol. 137, pages abstract.*

Collet et al., A binary plasmid system for shuffling combinatorial antibody libraries, 1992, PNAS, vol. 89, pp. 10026-10030.*

Loiler et al., Targeting recombinant adeno-associated virus vectors to enhance gene transfer to pancreatic islets and liver, 2003, Gene Therapy, vol. 10, pp. 1551-1558.*

Fang et al., Stable antibody expression at therapeutic levels using the 2A peptide, 2005, Nature Biotechnology, vol. 23, No. 5, pp. 584-590.*

Szymczak et al., Correction of multi-gene deficiency in vivo using a single 'self-cleaving' 2A peptide-based retroviral vector, 2004, Nature Biotechnology, vol. 22, No. 5, pp. 589-594.*

Altschul, Stephen F., et al., "Basic Local Alignment Search Tool," *Journal of Molecular Biology* (1990), vol. 215, pp. 403-410, Academic Press Limited, USA.

Bosselman, Robert A., et al., "Replication-Defective Chimeric Helper Proviruses and Factors Affecting Generation of Competent Virus: Expression of Moloney Murine Leukemia Virus Structural Genes via the Metallothionein Promoter," *Mollecular and Cellular Biology* (May 1987), vol. 7, No. 5, pp. 1797-1806, American Society for Microbiology, USA.

Capecchi, Mario R., "High Efficiency Transformation by Direct Microinjection of DNA into Cultured Mammalian Cells," *Cell* (Nov. 1980 (Part 2)), vol. 22, pp. 479-488, MIT, USA.

Chaplin, Paul J., et al., "Production of Interleukin-12 as a Self-Processing 2A Polypeptide," *Journal of Interferon and Cytokine Research* (1999), vol. 19, pp. 234-241.

Danos, Olivier and Mulligan, Richard C., "Safe and efficient generation of recombinant retroviruses with amphotropic and ecotropic host ranges," *Proc. Natl. Acad. Sci. USA* (Sep. 1988), vol. 85, pp. 6460-6464.

De Felipe, P., et al., "Use of the 2A sequence from foot-and-mouth disease virus in the generation of retroviral vectors for gene therapy," *Gene Therapy* (1999), vol. 6, pp. 198-208, Stockton Press, UK.

De Felipe, Pablo and Izquierdo, Marta, "Tricistronic and Tetracistronic Retroviral Vectors for Gene Transfer," *Human Gene Therapy* (Sep. 1, 2000), vol. 11, pp. 1921-1931.

Donnelly, Michelle L. L., et al., "The cleavage activities of aphthovirus and cardiovirus 2A proteins," *Journal of General Virology* (1997), vol. 78, pp. 13-21, UK.

Donnelly, Michelle L. L., et al., "Analysis of the aphthovirus 2A/2B polyprotein 'cleavage' mechanism indicates not a proteolytic reaction, but a novel translation effect: a putative ribosomal 'skip'," *Journal of General Virology* (2001), vol. 82, pp. 1013-1025, UK.

Donnelly, Michelle L. L., et al., "The 'cleavage' activities of foot-and-mouth disease virus 2A site-directed mutants and naturally occurring '2A-like' sequences," *Journal of General Virology* (2001), vol. 82, pp. 1027-1041, UK.

Duke, Gregory M., et al., "Sequence and Structural Elements That Contribute to Efficient Encephalomyocarditis Virus RNA Translation," *Journal of Virology* (Mar. 1992), vol. 66, No. 3, pp. 1602-1609.

Dull, Tom, et al., "A Third-Generation Lentivirus Vector with a Conditional Packaging System," *Journal of Virology* (Nov. 1998), vol. 72, No. 11, pp. 8463-8471.

Felgner, Philip L., et al., "Lipofection: A highly efficient, lipid-mediated DNA-transfection procedure," *Proc. Natl. Acad. Sci USA* (Nov. 1987), vol. 84, pp. 7413-7417.

Furler, S., et al., "Recombinant AAV vectors containing the foot and mouth disease virus 2A sequence confer efficient bicistronic gene expression in cultured cells and rat substantia nigra neurons," *Gene Therapy* (2001), vol. 8, pp. 864-873, Nature Publishing Group, USA.

Green, I.L., et al., "Antigen-specific human monoclonal antibodies from mice engineered with human Ig heavy and light chain YACs," *Nature Genetics* (May 1994), vol. 7, pp. 13-21, Nature Publishing Group, USA.

Guo, Zs, et al., "Evaluation of promoter strength for hepatic gene expression in vivo following adenovirus-mediated gene transfer," *Gene Therapy* (1996), vol. 3, pp. 802-810, Stockton Press, UK.

Halpin, Claire, et al., "Self-processing 2A-polyproteins—a system for co-ordinate express of multiple proteins in transgenic plants," *The Plant Journal* (1999), vol. 17(4), pp. 453-459, Blackwell Science Ltd., UK.

Hartley, Janet W. and Rowe, Wallace P., "Naturally occurring Murine Leukemia Viruses in Wild Mice: Characterization of a New 'Amphotropic' Class," *Journal of Virology* (Jul. 1976), vol. 19, No. 1, pp. 19-25.

Huez, Isabelle, et al., "Two Independent Internal Ribosome Entry Sites Are Involved in Translation Initiation of Vascular Endothelial Growth Factor mRNA," *Molecular and Cellular Biology* (Nov. 1998), Vo. 18, No. 11, pp. 6178-6190, American Society for Microbiology, USA.

Ill, Charles R., et al., "Optimization of the human factor VIII complementary DNA expression plasmid for gene therapy of hemophilia A," *Blood Coagulation and Fibrinolysis* (1997), vol. 8 (Suppl. 2), pp. S23-S30, Rapid Science Publishers, USA.

Jackson, Richard J. and Kaminski, Ann, "Internal initiation of translation in eukaryotes: The picornavirus paradigm and beyond," *RNA* (1995), vol. 1, pp. 985-1000, Cambridge University Press, USA.

Jackson, R. J., et al., "The Animal Picornavirus," *TIBS 15* (Dec. 1990), pp. 477-683, Elsevier Science Publishers Ltd., UK.

Jakobovitz, Aya, "Production and selection of antigen-specific fully human monoclonal antibodies from mice engineered with human Ig loci," *Advanced Drug Delivery Reviews* (1998), vol. 31, pp. 33-42, Elsevier Science B.V., UK.

Jakobovitz, Aya, "Production of fully human antibodies by transgenic mice," *Current Opinion in Biotechnology* (1995), vol. 6, pp. 561-566.

Kim, Dong Wan, et al., "Use of the human elongation factor lαpromoter as a versatile and efficient expression system," *Gene* (1990), vol. 91, pp. 212-213, Elsevier Science Publishers, B.V., UK.

Klein, T.M., et al., "High-velocity microprojectiles for delivering nucleic acids into living cells," *Nature* (May 7, 1987), vol. 327, pp. 70-73.

Knott, A., et al., "Tetracycline-Dependent Gene Regulation: Combinations of Transregulators Yield a Variety of Expression Windows," *BioTechniques* (2002), vol. 32, No. 4, pp. 797-806.

Köhler, G. and Milstein, C., "Derivation of specific antibody-producing tissue culture and tumor lines by cell fusion," *Eur. J. Immunol.* (1976), vol. 6, pp. 511-519.

Mannino, Raphael J. and Gould-Fogerite, Susan, "Liposome Mediated Gene Transfer," *Bio Techniques* (1988), vol. 6, No. 7, pp. 682-690.

Markowitz, Dina, et al., "A Safe Packaging Line for Gene Transfer: Separating Viral Genes on Two Different Plasmids," *Journal of Virology* (Apr. 1988), vol. 62, No. 4, pp. 1120-1124.

Miller, A. Dusty, "Human gene therapy comes of age," *Nature* (Jun. 11, 1992), vol. 357, pp. 455 to 460.

Miller, A. Dusty and Buttimore, Carol, "Redesign of Retrovirus Packaging Cell Lines to Avoid Recombination Leading to Helper Virus Production," *Molecular and Cellular Biology* (Aug. 1986), vol. 6, No. 8, pp. 2895-2902.

Miller, Dusty A. and Rosman, Guy J., "*Improved Retroviral Vectors for Gene Transfer and Expression*," *BioTechniques* (1989), vol. 7, No. 9, pp. 980-990.

Miyazaki, Jun-Ichi, et al., "Expression vector system based on the chicken β-actin promoter directs efficient production of interleukin-5," *Gene* (1989), vol. 79, pp. 269-277, Elsevier Science Publishers, B.V., UK.

Needleman, Saul B. and Wunsch, Christian D., "A general Mehtod Applicable to the Search for Similarities in the Amino Acid Sequence of Two Proteins," *Journal of Molecular Biology* (1970), Vo.. 48, pp. 443-453.

No, David, et al., "Ecdysone-inducible gene expression in mammalian cells and transgenic mice," *Proc. Natl. Acad. Sci. USA* (Apr. 1996), vol. 93, pp. 3346-3351.

Ory, Daniel S., "A stable human-derived packaging cell line for production of high titer retrovirus/vesicular stomatitis virus G pseudotypes," *Proc. Natl. Acad. Sci. USA* (Oct. 1996), vol. 93, pp. 11400-11406.

Osterwalder, Thomas, et al., "A conditional tissue-specific transgene expression system using inducible GAL4," *PNAS* (Oct. 23, 2001), vol. 98, No. 22, pp. 12596-12601.

Palmenberg, Ann C., "Proteolytic Processing of Picornaviral Polyprotein," *Annu. Rev. Microbiol.* (1990), vol. 44, pp. 603-623.

Pearson, William R., and Lipman, David J., "Improved tools for biological sequence comparison," *Proc. Natl. Acad. Sci. USA* (Apr. 1988), vol. 85, pp. 2444-2448.

Rivera, Victor M., "A humanized system for pharmacologic control of gene expression," *Nature Medicine* (Sep. 1996), vol. 2, No. 9, pp. 1028-1032.

Roosien, Jan, et al., Synthesis of foot-and-mouth disease virus capsid proteins in insect cells using baculovirus expression vectors, *Journal of General Virology* (1990), vol. 71, pp. 1703-1711, UK.

Ryan, Martin D. and Drew, Jeff, "Foot-and-mouth disease virus 2A oligopeptide mediated cleavage of an artificial protein," *The EMBO Journal* (1994), vol. 13, No. 4, pp. 928-933, Oxford University Press, UK.

Ryan, Martin D., et al., "Cleavage of foot-and-mouth disease virus polyprotein is mediated by residues located within a 19 amino acid sequence," *Journal of General Virology* (1991), vol. 72, pp. 2727-2732, UK.

Ryan, Martin D., et al., "Specificity of Enzyme-Substrate Interactions in Foot-and-Mouth Disease Virus Polyprotein Processing," *Virology* (1989), vol. 173, pp. 35-45.

Shigekawa, Katherine and Dower, William J., "Electroporation of Eukaryotes and Prokaryotes: A General Approach to the Introduction of Macromolecules into Cells," *Bio Techniques* (1988), vol. 6, No. 8, pp. 742-751.

Smith, Temple F. and Waterman, Michael S., "Comparison of Biosequences," *Advances In Applied Mathematics* (1981), vol. 2, pp. 482-489.

Suhr, Steven T., et al., "High level transactivation by a modified Bombyx ecdysone receptor in mammalian cells without exogenous retinoid X receptor," *Proc. Natl. Acad. Sci. USA* (Jul. 1998), vol. 95, pp. 7999-8004.

Vakharia, Vikram N., et al., "Proteolytic Processing of Foot-and-Mouth Disease Virus Polyproteins Expressed in a Cell-Free System from Clone-Derived Transcripts," *Journal of Virology* (Oct. 1987); vol. 61, No. 10, pp. 3199-3207.

Van Der Velden, Alike W. and Thomas, Adri A.M., "The role of the 5' untranslated region of an mRNA in translation regulation during development," *The International Journal of Biochemistry & Cell Biology* (1999), vol. 31, pp. 87-106.

Ye, Xuehai, et al., "Regulated Delivery of Therapeutic Proteins After in Vivo Somatic Cell Gene Transfer," *Science* (Jan. 1, 1999), vol. 283, pp. 88-91.

Zennou, Véronique, et al., "HIV-1 Genome Nuclear Import Is Mediated by a Central DNA Flap, " *Cell* (Apr. 14, 2000), vol. 101, pp. 173-185.

Zufferey, Romain, et al., "Self-Inactivating Lentivirus Vector for Safe and Efficient in Vivo Gene Delivery," *Journal of Virology* (Dec. 1998), vol. 72, No. 12, pp. 9873-9880, USA.

Zufferey, Romain, et al., "Multiply attenuated lentiviral vector achieves efficient gene delivery in vivo," *Nature Biotechnology* (Sep. 1997), vol. 15, pp. 871-875.

International Search Report for application No. PCT/US2006/027949.

Li et al., A hepatocellular carcinoma-specific adenovirus variant, CV890, eliminates distant human liver tumors in combination with doxorubicin, Cancer Res. 61:6428- 6436 (2001).

Chazenbalk et al., 1996, "Evidence for negative cooperativity among human thyrotropin receptors overexpressed in mammalian cells," Endocrinology 137:4586-4591.

Green, 1999, "Antibody engineering via genetic engineering of the mouse: Xenomouse strains are a vehicle for the facile generation of therapeutic human monoclonal antibodies," J. Immunol. Methods 231:11-23.

Hamstra and Rehemtulla, 1999, "Toward and Enzyme/Prodrug Strategy for Cancer Gene Therapy: Endogenous Activation of Carboxypeptidase A Mutants by the PACE/Furin Family of Propeptidases," Human Gene Therapy 10:235-248.

Lamikarna et al., 2005, "In vivo evaluation of an EIAV vector for the systemic genetic delivery of therapeutic antibodies," Gene Therapy 12:988-998.

Nakai et al., 1998, "Adeno-Associated Viral Vector-Mediated Gene Transfer of Human Blood Coagulation Factor IX Into Mouse Liver," Blood 91(12):4600-4607.

O'Rourke et al., 2002, "Comparison of gene transfer efficiencies and gene expression levels achieved with equine infectious anemia virus- and human immunodeficiency virus type 1- derived lentivirus vectors," J. Virol. 76(3):1510-1515.

Paulas, 1998, "Protein Splicing: A Novel Form of Gene Expression and Paradigm for Self-Catalyzed Protein Rearrangements", Pure & Appl. Chem., 70(1): 1-8.

Xu, 2001, "Optimization of Transcriptional Regulatory Elements for Constructing Plasmid Vecors", Gene 272:149-156.

Auricchio et al., "Pharmacological Regulation of Protein Expression from Adeno-Associated Viral Vectors in the Eye," *Mol. Ther.*, 6:238-242 (2002).

Bossis and Chiorini, "Cloning of an Avian-Associated Virus (AAAV) and Generation of Recombinant AAAV Particles," *J. Virol.*, 77:6799-68 10 (2003).

Burton et al., "Coexpression of Factor VIII Heavy and Light Chain Adeno-Associated Viral Vectors Produces Biologically Active Protein," *PNAS*, 96:12725-12730 (1999).

Costa et al., "The Cell-Specific Enhancer of the Mouse Transthyretin (Prealbumin) Gene Binds a Common Factor at One Site and a Liver-Specific Factor(s) at Two Other Sites," *Mol. Cell Biol.*, 8:81-90 (1988).

Davidson et al., "Recombinant Adeno-Associated Virus type 2, 4, and 5 Vectors: Transduction of Variant Cell Types and Regions in the Mammalian Central Nervous System," *PNAS USA*, 97:3428-32 (2000).

Galanis et al., "Phase II Trial of Temsirolimus (CCI-779) in Recurrent Glioblastoma Multiforme: A North Central Cancer Treatment Group Study," *J. Clin. Oncol*,. 23:5294-5304 (2005).

Gao et al., "Novel Adeno-Associated Viruses from Rhesus Monkeys as Vectors for Human Gene Therapy," *PNAS USA*, 99: 11854-11859 (2002).

Gao et al., "Adeno-Associated Viruses Undergo Substantial Evolution in Primates During Natural Infections," *PNAS USA*, 100: 6081-6086 (2003).

McCarty et al., "Self-Complementary Recombinant Adeno-Associated Virus (scAAV) Vectors Promote Efficient Transduction Independently of DNA Synthesis," *Gene Ther.*, 8:1248-1254 (2001).

Passini et al., "Intraventricular Brain Injection of Adeno-Associated Virus Type 1 (AAV1) in Neonatal Mice Results in Complementary Patterns of Neuronal Transduction to AAV2 and total Long-Term Correction of Storage Lesions in the Brains of β-Glucuronidase-Deficient Mice," *J. Virol.*, 77:7034-7040 (2003).

Plate et al., "Vascular Endothelial Growth Factor is a Potential Tumour Angiogenesis Factor in Human Gliomas in Vivo," *Nature*, 359:845-848 (1992).

Rivera et al., "Long-Term Pharmacologically Regulated Expression of Erythropoietin in Primates following AAV-mediated gene transfer," *Blood*, 105;1424-1430 (2005).

Rivera et al., "Long-Term Regulated Expression of Growth Hormone in Mice after Intramuscular Gene Transfer," *PNAS USA*, 96:8657-8662 (.1999).

* cited by examiner

SEQUENCE LISTING

<160> NUMBER OF SEQ ID NOS: 19

<210> SEQ ID NO 1
<211> LENGTH: 19
<212> TYPE: PRT
<213> ORGANISM: Foot-and-mouth disease virus

<400> SEQUENCE: 1

Leu Leu Asn Phe Asp Leu Leu Lys Leu Ala Gly Asp Val Glu Ser Asn
 1               5                  10                  15

Pro Gly Pro

-continued

```
<210> SEQ ID NO 2
<211> LENGTH: 19
<212> TYPE: PRT
<213> ORGANISM: Foot-and-mouth disease virus

<400> SEQUENCE: 2

Thr Leu Asn Phe Asp Leu Leu Lys Leu Ala Gly Asp Val Glu Ser Asn
 1               5                  10                  15

Pro Gly Pro

<210> SEQ ID NO 3
<211> LENGTH: 14
<212> TYPE: PRT
<213> ORGANISM: Foot-and-mouth disease virus

<400> SEQUENCE: 3

Leu Leu Lys Leu Ala Gly Asp Val Glu Ser Asn Pro Gly Pro
 1               5                  10

<210> SEQ ID NO 4
<211> LENGTH: 17
<212> TYPE: PRT
<213> ORGANISM: Foot-and-mouth disease virus

<400> SEQUENCE: 4

Asn Phe Asp Leu Leu Lys Leu Ala Gly Asp Val Glu Ser Asn Pro Gly
 1               5                  10                  15

Pro

<210> SEQ ID NO 5
<211> LENGTH: 20
<212> TYPE: PRT
<213> ORGANISM: Foot-and-mouth disease virus

<400> SEQUENCE: 5

Gln Leu Leu Asn Phe Asp Leu Leu Lys Leu Ala Gly Asp Val Glu Ser
 1               5                  10                  15

Asn Pro Gly Pro
            20

<210> SEQ ID NO 6
<211> LENGTH: 24
<212> TYPE: PRT
<213> ORGANISM: Foot-and-mouth disease virus

<400> SEQUENCE: 6

Ala Pro Val Lys Gln Thr Leu Asn Phe Asp Leu Leu Lys Leu Ala Gly
 1               5                  10                  15

Asp Val Glu Ser Asn Pro Gly Pro
            20

<210> SEQ ID NO 7
<211> LENGTH: 58
<212> TYPE: PRT
<213> ORGANISM: Foot-and-mouth disease virus

<400> SEQUENCE: 7

Val Thr Glu Leu Leu Tyr Arg Met Lys Arg Ala Glu Thr Tyr Cys Pro
 1               5                  10                  15

Arg Pro Leu Leu Ala Ile His Pro Thr Glu Ala Arg His Lys Gln Lys
            20                  25                  30
```

-continued

```
Ile Val Ala Pro Val Lys Gln Thr Leu Asn Phe Asp Leu Leu Lys Leu
        35                  40                  45
Ala Gly Asp Val Glu Ser Asn Pro Gly Pro
    50                  55

<210> SEQ ID NO 8
<211> LENGTH: 40
<212> TYPE: PRT
<213> ORGANISM: Foot-and-mouth disease virus

<400> SEQUENCE: 8

Leu Leu Ala Ile His Pro Thr Glu Ala Arg His Lys Gln Lys Ile Val
1               5                   10                  15

```
<400> SEQUENCE: 12

Leu Ala Gly Phe Ala Thr Val Ala Gln Ala
 1               5                  10

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Leu Val Pro Arg Gly Ser
 1               5

<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Arg Lys Lys Arg
 1

<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Arg Lys Arg Arg
 1

<210> SEQ ID NO 16
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Arg Arg Lys Arg
 1

<210> SEQ ID NO 17
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Arg Arg Arg Arg
 1

<210> SEQ ID NO 18
<211> LENGTH: 4
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Arg Ala Lys Arg
 1

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Variable amino acid

<400> SEQUENCE: 19

Arg Xaa Arg Lys Arg
 1               5
```

METHODS TO EXPRESS RECOMBINANT PROTEINS FROM LENTIVIRAL VECTORS

CROSS-REFERENCE TO RELATED APPLICATIONS

This application claims the priority benefit of U.S. Provisional Patent Application No. 60/700,298, filed Jul. 19, 2005. The priority application is expressly incorporated by reference herein in its entirety.

BACKGROUND OF THE INVENTION

1. Field of the Invention

The invention relates to novel lenti vector constructs designed to express recombinant full-length proteins or fragments thereof. The lenti constructs may be used for ex vivo or in vivo expression of a heterologous protein coding sequence by a cell or organ, or in vitro for the production of recombinant proteins by lenti vector-transduced cells.

2. Background of the Technology

Recombinant proteins as therapeutic modalities have found increasing use in recent years. Numerous recombinant protein-based therapies are in various stages of clinical development. One limitation to widespread clinical application of recombinant protein technology is the difficulty in production of proteins that include two or more coding sequences or domains such that the domains are expressed in the proper ratio with appropriate post-translational processing resulting in production of a functional heterodimeric molecule. A further limitation is the high cost associated with the ability to produced adequate levels of protein for clinical applications.

Monoclonal antibodies have been proven as effective therapeutics for cancer and other diseases. Current antibody therapy often involves repeat administration and long term treatment regimens, which are associated with a number of disadvantages, such as inconsistent serum levels, limited duration of efficacy per administration such that frequent readministration is required and high cost. The use of antibodies as diagnostic tools and therapeutic modalities has also found increasing use in recent years. One limitation to the widespread clinical application of antibody technology is that typically large amounts of antibody are required for therapeutic efficacy and the costs associated with production are significant. Chinese Hamster Ovarian (CHO) cells, SP20 and NSO2 myeloma cells are the most commonly used mammalian cell lines for commercial scale production of glycosylated human proteins such as antibodies. The yields obtained from mammalian cell line production typically range from 50-250 mg/L for 5-7 day culture in a batch fermentor or 300-1000 mg/L for 7-12 day cultures in fed batch fermentors. High-level production often relies upon gene amplification and selection of best performing clones that is time consuming and further increases the cost of development and production. In addition, stability issues with respect to antibody-producing cell lines are often evident following multiple passages.

Previous attempts to express full length recombinant proteins with two or more domains or chains (and thus two or more coding sequences or open reading frames (ORFs)) via recombinant DNA technology have met with limited success, typically resulting in unequal levels of expression of the two or more domains or chains of the protein or polypeptide and more importantly, a lower level of expression for the second coding sequence. In order to obtain optimal expression of a fully functional and biologically active protein or polypeptide that has two or more domains, substantially equimolar expression of the two or more domains is required. Conventional vectors that rely on dual promoter regulation of gene expression are invariably affected by promoter interaction (i.e., promoter interference) that may compromise equimolar or substantially equimolar expression of the genes.

Lentiviral vectors are a type of retroviral vector that can infect both dividing and non-dividing cells. They can be used to express protein from non-dividing or terminally differentiated cells such as neurons, macrophages, hematopoietic stem cells, retinal photoreceptors, muscle and liver cells, cell types for which other vector systems cannot be used effectively.

There remains a need for improved gene expression systems for production of recombinant proteins and polypeptides, in particular proteins and polypeptides that have two or more domains or chains, such that sufficient expression of a biologically active recombinant protein or polypeptide is achieved at commercially reasonable cost.

The present invention addresses this need by demonstrating the feasibility and use of lentivector constructs for the expression of functional recombinant proteins and polypeptides which have two or more domains.

SUMMARY OF THE INVENTION

The present invention provides lentivector constructs for expression of protein or polypeptide open reading frames from a single cell and methods of using the same.

In one preferred approach, the vectors have a self-processing cleavage sequence between the protein or polypeptide coding sequences allowing for expression of more than one functional protein or polypeptide using a single promoter. The invention finds utility in production of two or more proteins or polypeptides or a protein or polypeptide having two or more domains (or chains) using a lentiviral vector where sustained expression occurs in a single cell. Exemplary lentivector constructs comprise a self-processing cleavage sequence and may further comprise an additional proteolytic cleavage site for removal of the self-processing cleavage sequence from the expressed protein or polypeptide. The vector constructs find utility in methods relating to enhanced production of biologically active proteins, polypeptides or fragments thereof, in vitro and in vivo.

The invention relates to engineered lentiviral vectors that encode two or more domains or chains of a multimeric protein. In one aspect the multimeric protein is an immunoglobulin (i.e., an antibody) and full-length antibody heavy and light chain coding sequences are expressed using a lentivector comprising a single open reading frame driven by a single promoter wherein the vector comprises a self processing cleavage site or sequence between the heavy and light chain coding sequences. In another aspect the protein is a multimeric protein and the full-length coding sequences are expressed using a lentivector comprising a single open reading frame driven by a single promoter wherein the vector comprises a self-processing cleavage site or sequence.

In yet another aspect, the invention relates to a method for high level expression of recombinant protein using more than one engineered lentiviral vector wherein each lentivector encodes a single open reading frame of a multimeric protein driven by a single promoter. For example, for expression of a full-length antibody, individual lentivectors that encode the full-length antibody heavy and light chain, respectively, are used to infect the same cell such that high level expression of a biologically active antibody results.

DETAILED DESCRIPTION OF THE INVENTION

Figure 1:
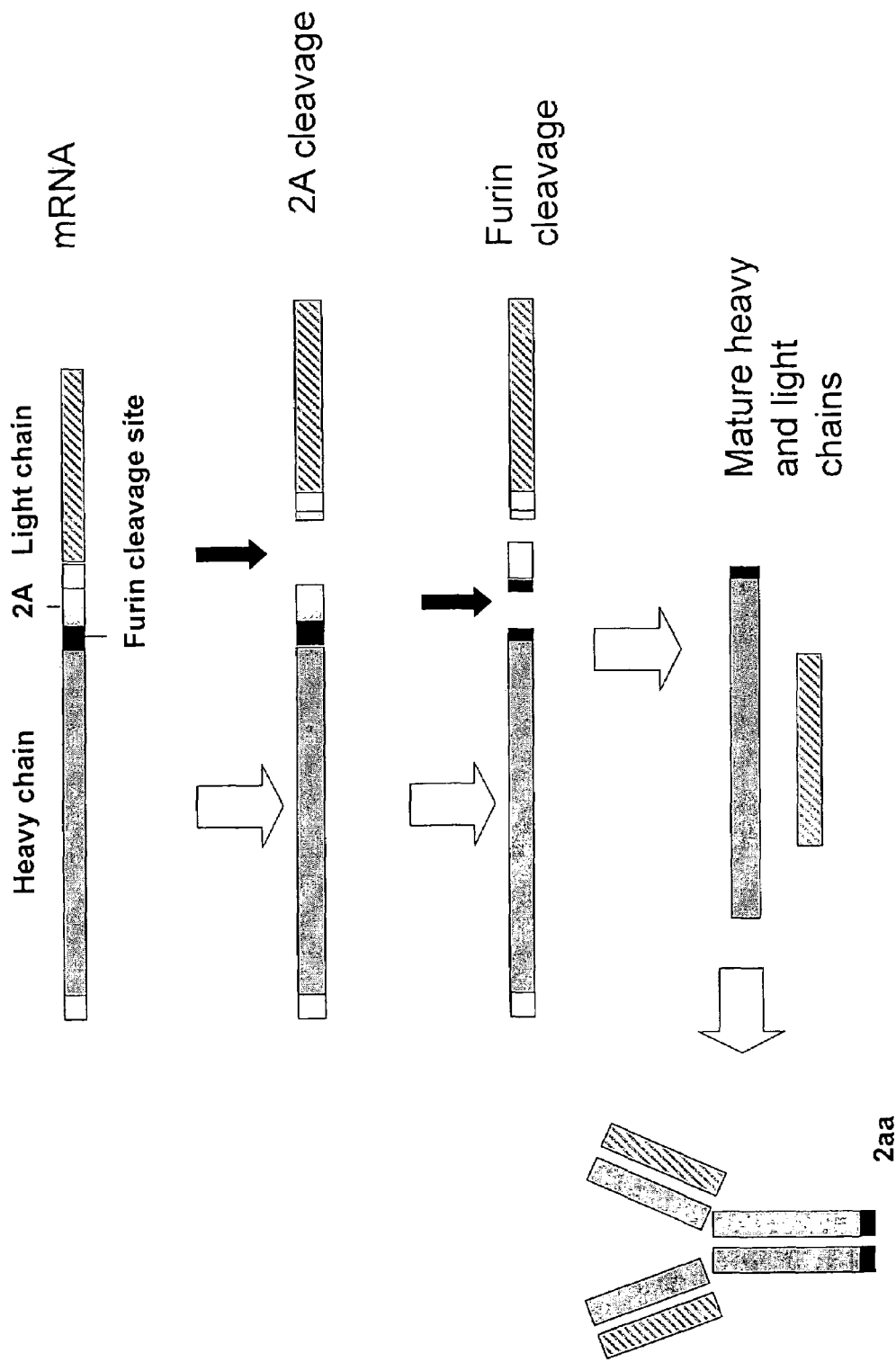
FIG. 1 is a schematic depiction of the process for expression of a full-length immunoglobulin (antibody) using constructs that include a self-processing cleavage site, such as 2A, and a furin cleavage site.

The various compositions and methods of the invention are described below. Although particular compositions and methods are exemplified herein, it is understood that any of a number of alternative compositions and methods are applicable and suitable for use in practicing the invention. It will also be understood that an evaluation of the protein or polypeptide expression constructs (vectors) and methods of the invention may be carried out using procedures standard in the art.

The practice of the present invention will employ, unless otherwise indicated, conventional techniques of cell biology, molecular biology (including recombinant techniques), microbiology, biochemistry and immunology, which are known to those of skill in the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology" (D. M. Weir & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction", (Mullis et al., eds., 1994); and "Current Protocols in Immunology" (J. E. Coligan et al., eds., 1991).

DEFINITIONS

Unless otherwise indicated, all terms used herein have the same meaning as they would to one skilled in the art and the practice of the present invention will employ, conventional techniques of microbiology and recombinant DNA technology, which are within the knowledge of those of skill of the art.

The term "vector", as used herein, refers to a DNA or RNA molecule such as a plasmid, virus or other vehicle, which contains one or more heterologous or recombinant DNA sequences and is designed for transfer between different host cells. The terms "expression vector" and "gene therapy vector" refer to any vector that is effective to incorporate and express heterologous DNA fragments in a cell. A cloning or expression vector may comprise additional elements, for example, the expression vector may have two replication systems, thus allowing it to be maintained in two organisms, for example in human cells for expression and in a prokaryotic host for cloning and amplification. Any suitable vector can be employed that is effective for introduction of nucleic acids into cells such that protein or polypeptide expression results, e.g. a viral vector or non-viral plasmid vector. Any cells effective for expression, e.g., insect cells and eukaryotic cells such as yeast or mammalian cells are useful in practicing the invention.

The terms "heterologous DNA" and "heterologous RNA" refer to nucleotides that are not endogenous (native) to the cell or part of the genome in which they are present. Generally heterologous DNA or RNA is added to a cell by transduction, infection, transfection, transformation or the like, as further described below. Such nucleotides generally include at least one coding sequence, but the coding sequence need not be expressed. The term "heterologous DNA" may refer to a "heterologous coding sequence" or a "transgene".

As used herein, the terms "protein" and "polypeptide" may be used interchangeably and typically refer to "proteins" and "polypeptides" of interest that are expresses using the self processing cleavage site-containing vectors of the present invention. Such "proteins" and "polypeptides" may be any protein or polypeptide useful for research, diagnostic or therapeutic purposes, as further described below.

The term "replication defective" as used herein relative to a viral gene therapy vector of the invention means the viral vector cannot independently further replicate and package its genome. For example, when a cell of a subject is infected with rAAV virions, the heterologous gene is expressed in the infected cells, however, due to the fact that the infected cells lack AAV rep and cap genes and accessory function genes, the rAAV is not able to replicate.

As used herein, a "retroviral transfer vector" refers to an expression vector that comprises a nucleotide sequence that encodes a transgene and further comprises nucleotide sequences necessary for packaging of the vector. Preferably, the retroviral transfer vector also comprises the necessary sequences for expressing the transgene in cells.

As used herein, "packaging system" refers to a set of viral constructs comprising genes that encode viral proteins involved in packaging a recombinant virus. Typically, the constructs of the packaging system will ultimately be incorporated into a packaging cell.

As used herein, a "second generation" lentiviral vector system refers to a lentiviral packaging system that lacks functional accessory genes, such as one from which the accessory genes, vif, vpr, vpu and nef, have been deleted or inactivated. See, e.g., Zufferey et al., 1997, Nat. Biotechnol. 15:871-875.

As used herein, a "third generation" lentiviral vector system refers to a lentiviral packaging system that has the characteristics of a second generation vector system, and further lacks a functional tat gene, such as one from which the tat gene has been deleted or inactivated. Typically, the gene encoding rev is provided on a separate expression construct. See, e.g., Dull et al., 1998, J. Virol. 72(11):8463-8471.

As used herein, "pseudotyped" refers to the replacement of a native envelope protein with a heterologous or functionally modified envelope protein.

The term "operably linked" as used herein relative to a recombinant DNA construct or vector means nucleotide components of the recombinant DNA construct or vector are functionally related to one another for operative control of a selected coding sequence. Generally, "operably linked" DNA sequences are contiguous, and, in the case of a secretory leader, contiguous and in reading frame. However, enhancers do not have to be contiguous.

As used herein, the term "gene" or "coding sequence" means the nucleic acid sequence which is transcribed (DNA) and translated (mRNA) into a polypeptide in vitro or in vivo when operably linked to appropriate regulatory sequences. The gene may or may not include regions preceding and following the coding region, e.g. 5' untranslated (5' UTR) or "leader" sequences and 3' UTR or "trailer" sequences, as well as intervening sequences (introns) between individual coding segments (exons).

A "promoter" is a DNA sequence that directs the binding of RNA polymerase and thereby promotes RNA synthesis, i.e., a minimal sequence sufficient to direct transcription. Promoters and corresponding protein or polypeptide expression may be cell-type specific, tissue-specific, or species specific. Also included in the nucleic acid constructs or vectors of the invention are enhancer sequences that may or may not be contiguous with the promoter sequence. Enhancer sequences influence promoter-dependent gene expression and may be located in the 5' or 3' regions of the native gene.

"Enhancers" are cis-acting elements that stimulate or inhibit transcription of adjacent genes. An enhancer that inhibits transcription also is termed a "silencer". Enhancers can function (i.e., can be associated with a coding sequence) in either orientation, over distances of up to several kilobase pairs (kb) from the coding sequence and from a position downstream of a transcribed region.

A "regulatable promoter" is any promoter whose activity is affected by a cis or trans acting factor (e.g., an inducible promoter, such as an external signal or agent).

A "constitutive promoter" is any promoter that directs RNA production in many or all tissue/cell types at most times, e.g., the human CMV immediate early enhancer/promoter region which promotes constitutive expression of cloned DNA inserts in mammalian cells.

The terms "transcriptional regulatory protein", "transcriptional regulatory factor" and "transcription factor" are used interchangeably herein, and refer to a nuclear protein that binds a DNA response element and thereby transcriptionally regulates the expression of an associated gene or genes. Transcriptional regulatory proteins generally bind directly to a DNA response element, however in some cases binding to DNA may be indirect by way of binding to another protein that in turn binds to, or is bound to a DNA response element.

As used herein, the term "sequence identity" means nucleic acid or amino acid sequence identity between two or more aligned sequences, when aligned using a sequence alignment program. The terms "% homology" and "% identity" are used interchangeably herein and refer to the level of nucleic acid or amino acid sequence identity between two or more aligned sequences, when aligned using a sequence alignment program. For example, 80% homology means the same thing as 80% sequence identity determined by a defined algorithm under defined conditions.

The terms "identical" or percent "identity" in the context of two or more nucleic acid or protein sequences, refer to two or more sequences or subsequences that are the same or have a specified percentage of amino acid residues or nucleotides that are the same, when compared and aligned for maximum correspondence, as measured using one of the sequence comparison algorithms described herein, e.g. the Smith-Waterman algorithm, or by visual inspection.

As used herein, an "internal ribosome entry site" or "IRES" refers to an element that promotes direct internal ribosome entry to the initiation codon, such as ATG, of a cistron (a protein encoding region), thereby leading to the cap-independent translation of the gene. See, e.g., Jackson R J, Howell M T, Kaminski A (1990) Trends Biochem Sci 15(12):477-83) and Jackson R J and Kaminski, A. (1995) RNA 1(10):985-1000. The examples described herein are relevant to the use of any IRES element, which is able to promote direct internal ribosome entry to the initiation codon of a cistron. "Under translational control of an IRES" as used herein means that translation is associated with the IRES and proceeds in a cap-independent manner.

A "self-processing cleavage site" or "self-processing cleavage sequence" is defined herein as a post-translational or co-translational processing cleavage site or sequence. Such a "self-processing cleavage" site or sequence refers to a DNA or amino acid sequence, exemplified herein by a 2A site, sequence or domain or a 2A-like site, sequence or domain. As used herein, a "self-processing peptide" is defined herein as the peptide expression product of the DNA sequence that encodes a self-processing cleavage site, sequence or domain, which upon translation mediates rapid intramolecular (cis) cleavage of a protein or polypeptide comprising the self-processing cleavage site to yield discrete mature protein or polypeptide products.

As used herein, the term "additional proteolytic cleavage site", refers to a sequence which is incorporated into an expression construct of the invention adjacent a self-processing cleavage site, such as a 2A or 2A like sequence, and provides a means to remove additional amino acids that remain following cleavage by the self processing cleavage sequence. Exemplary "additional proteolytic cleavage sites" are described herein and include, but are not limited to, furin cleavage sites with the consensus sequence RXK(R)R (SEQ ID NO: 10). Such furin cleavage sites can be cleaved by endogenous subtilisin-like proteases, such as furin and other serine proteases within the protein secretion pathway.

As used herein, the terms "immunoglobulin" and "antibody" may be used interchangeably and refer to intact immunoglobulin or antibody molecules as well as fragments thereof, such as Fa, F (ab')2, and Fv, which are capable of binding an antigenic determinant. Such an "immunoglobulin" and "antibody" is composed of two identical light polypeptide chains of molecular weight approximately 23,000 daltons, and two identical heavy chains of molecular weight 53,000-70,000. The four chains are joined by disulfide bonds in a "Y" configuration. Heavy chains are classified as gamma (IgG), mu (IgM), alpha (IgA), delta (IgD) or epsilon (IgE) and are the basis for the class designations of immunoglobulins, which determines the effector function of a given antibody. Light chains are classified—as either kappa or lambda. When reference is made herein to an "immunoglobulin or fragment thereof", it will be understood that such a "fragment thereof" is an immunologically functional immunoglobulin fragment.

The term "humanized antibody" refers to an antibody molecule in which one or more amino acids of the antigen binding regions of a non-human antibody have been replaced in order to more closely resemble a human antibody, while retaining the binding activity of the original non-human antibody. See, e.g., U.S. Pat. No. 6,602,503.

The term "antigenic determinant", as used herein, refers to that fragment of a molecule (i.e., an epitope) that makes contact with a particular antibody. Numerous regions of a protein or fragment of a protein may induce the production of antibodies that binds specifically to a given region of the three-dimensional structure of the protein. These regions or structures are referred to as antigenic determinants. An antigenic determinant may compete with the intact antigen (i.e., the immunogen used to elicit the immune response) for binding to an antibody.

The term "fragment," when referring to a recombinant protein or polypeptide of the invention means a polypeptide which has an amino acid sequence which is the same as part of, but not all of, the amino acid sequence of the corresponding full length protein or polypeptide, and which retains at least one of the functions or activities of the corresponding full length protein or polypeptide. The fragment preferably includes at least 20-100 contiguous amino acid residues of the full-length protein or polypeptide.

The terms "administering" or "introducing", as used herein refer to delivery of a vector for recombinant protein expression to a cell or to cells and/or organs of a subject. Such administering or introducing may take place in vivo, in vitro or ex vivo. A vector for recombinant protein or polypeptide expression may be introduced into a cell by transfection, which typically means insertion of heterologous DNA into a cell by physical means (e.g., calcium phosphate transfection, electroporation, microinjection or lipofection); infection, which typically refers to introduction by way of an infectious agent, i.e. a virus; or transduction, which typically means stable infection of a cell with a virus or the transfer of genetic material from one microorganism to another by way of a viral agent (e.g., a bacteriophage).

"Transformation" is typically used to refer to bacteria comprising heterologous DNA or cells that express an oncogene and have therefore been converted into a continuous growth mode such as tumor cells. A vector used to "transform" a cell may be a plasmid, virus or other vehicle.

Typically, a cell is referred to as "transduced", "infected", "transfected" or "transformed" dependent on the means used for administration, introduction or insertion of heterologous DNA (i.e., the vector) into the cell. The terms "transduced", "transfected" and "transformed" may be used interchangeably herein regardless of the method of introduction of heterologous DNA. A cell may be "transduced" by infection with a viral vector.

As used herein, the terms "stably transformed", "stably transfected" and "transgenic" refer to cells that have a non-native (heterologous) nucleic acid sequence integrated into the genome. Stable transfection is demonstrated by the establishment of cell lines or clones comprised of a population of daughter cells containing the transfected DNA stably integrated into their genomes. In some cases, "transfection" is not stable, i.e., it is transient. In the case of transient transfection, the exogenous or heterologous DNA is expressed, however, the introduced sequence is not integrated into the genome and is considered to be episomal.

As used herein, "ex vivo administration" refers to a process where primary cells are taken from a subject, a vector is administered to the cells to produce transduced, infected or transfected recombinant cells and the recombinant cells are readministered to the same or a different subject.

A "multicistronic transcript" refers to an mRNA molecule that contains more than one protein coding region, or cistron. An mRNA comprising two coding regions is denoted a "bicistronic transcript." The "5'-proximal" coding region or cistron is the coding region whose translation initiation codon (usually AUG) is closest to the 5'-end of a multicistronic mRNA molecule. A "5'-distal" coding region or cistron is one whose translation initiation codon (usually AUG) is not the closest initiation codon to the 5' end of the mRNA. The terms "5'-distal" and "downstream" are used synonymously to refer to coding regions that are not adjacent to the 5' end of an mRNA molecule.

As used herein, "co-transcribed" means that two (or more) coding regions or polynucleotides are under transcriptional control of a single transcriptional control or regulatory element.

The term "host cell", as used herein refers to a cell that has been transduced, infected, transfected or transformed with a vector. The vector may be a plasmid, a viral particle, a phage, etc. The culture conditions, such as temperature, pH and the like, are those previously used with the host cell selected for expression, and will be apparent to those skilled in the art. It will be appreciated that the term "host cell" refers to the original transduced, infected, transfected or transformed cell and progeny thereof.

As used herein, the terms "biological activity" and "biologically active", refer to the activity attributed to a particular protein in a cell line in culture or in a cell-free system, such as a ligand-receptor assay in ELISA plates. The "biological activity" of an "immunoglobulin", "antibody" or fragment thereof refers to the ability to bind an antigenic determinant and thereby facilitate immunological function.

As used herein, the terms "tumor" and "cancer" refer to a cell that exhibits a loss of growth control and forms unusually large clones of cells. Tumor or cancer cells generally have lost contact inhibition and may be invasive and/or have the ability to metastasize.

Internal Ribosome Entry Site (IRES)

IRES elements were first discovered in picornavirus mRNAs (Jackson R J, Howell M T, Kaminski A (1990) *Trends Biochem Sci* 15(12):477-83) and Jackson R J and Kaminski, A. (1995) *RNA* 1(10):985-1000). Examples of IRES generally employed by those of skill in the art include those described in U.S. Pat. No. 6,692,736. Examples of "IRES" known in the art include, but are not limited to IRES obtainable from picornavirus (Jackson et al., 1990) and IRES obtainable from viral or cellular mRNA sources, such as for example, immunoglobulin heavy-chain binding protein (BiP), the vascular endothelial growth factor (VEGF) (Huez et al. (1998) Mol. Cell. Biol. 18(11):6178-6190), the fibroblast growth factor 2 (FGF-2), and insulin-like growth factor (IGFII), the translational initiation factor eIF4G and yeast transcription factors TFIID and HAP4, the encephelomy-carditis virus (EMCV) which is commercially available from Novagen (Duke et al. (1992) *J. Virol* 66(3):1602-9) and the VEGF IRES (Huez et al. (1998) *Mol Cell Biol* 18(11):6178-90). IRES have also been reported in different viruses such as cardiovirus, rhinovirus, aphthovirus, HCV, Friend murine leukemia virus (FrMLV) and Moloney murine leukemia virus (MoMLV). As used herein, "IRES" encompasses functional variations of IRES sequences as long as the variation is able to promote direct internal ribosome entry to the initiation codon of a cistron. An IRES may be mammalian, viral or protozoan.

The IRES promotes direct internal ribosome entry to the initiation codon of a downstream cistron, leading to cap-independent translation. Thus, the product of a downstream cistron can be expressed from a bicistronic (or multicistronic) mRNA, without requiring either cleavage of a polyprotein or generation of a monocistronic mRNA. Internal ribosome entry sites are approximately 450 nucleotides in length and are characterized by moderate conservation of primary sequence and strong conservation of secondary structure. The most significant primary sequence feature of the IRES is a pyrimidine-rich site whose start is located approximately 25 nucleotides upstream of the 3' end of the IRES. See Jackson et al. (1990).

In eukaryotic cells, translation is normally initiated by the ribosome scanning from the capped mRNA 5' end, under the control of initiation factors. However, several cellular mRNAs have been found to have IRES structure to mediate the cap-independent translation (van der Velde, et al. (1999) *Int J Biochem Cell Biol.* 31:87-106. An IRES sequence may be tested and compared to a 2A sequence as shown in Example 1. In one exemplary protocol a test vector or plasmid is generated with one transgene, such as PF-4 or VEGF-TRAP, placed under translational control of an IRES, 2A or 2A-like sequence to be tested. A cell is transfected with the vector or plasmid containing the IRES- or 2A-reporter gene sequences and an assay is performed to detect the presence of the transgene. In one illustrative example, the test plasmid comprises co-transcribed PF-4 and VEGF-TRAP coding sequences transcriptionally driven by a CMV promoter wherein the PF-4 or VEGF-TRAP coding sequence is translationally driven by the IRES, 2A or 2A-like sequence to be tested. Host cells are transiently transfected with the test vector or plasmid by means known to those of skill in the art and assayed for the expression of the transgene.

For some time, in order to express two or more proteins from a single viral or non-viral vector, an internal ribosome entry site (IRES) sequence has been commonly used to drive expression of the second, third, fourth gene, etc. Although the use of IRES is considered to be the state of the art by many, when two genes are linked via IRES, the expression level of the second gene is often significantly reduced (Furler et al., Gene Therapy 8:864-873 (2001)). In fact, the use of an IRES to control transcription of two or more genes operably linked to the same promoter can result in lower level expression of the second, third, etc. gene relative to the gene adjacent the promoter. In addition, an IRES sequence may be sufficiently long to present issues with the packaging limit of the vector, e.g., the eCMV IRES has a length of 507 base pairs.

The present invention provides advantages over the use of an IRES in that a vector for recombinant protein or polypeptide expression comprising a self-processing peptide (exemplified herein by 2A peptides) facilitates expression of two or more protein or polypeptide coding sequences using a single promoter, wherein the two or more proteins or polypeptides are expressed in a substantially equimolar ratio.

Self-Processing Cleavage Sites or Sequences

The linking of proteins in the form of polyproteins in a single open reading frame is a strategy adopted in the replication of many viruses including picornaviridae. Upon translation, virus-encoded proteinases mediate rapid intramolecular (cis) cleavage of a polyprotein to yield discrete mature protein products. Foot and Mouth Disease viruses (FMDV) are a group within the picornaviridae that express a single, long open reading frame encoding a polyprotein of approximately 225 kD. The full length translation product undergoes rapid intramolecular (cis) cleavage at the C-terminus of a self-processing cleavage site, for example, a 2A site or region, located between the capsid protein precursor (P1-2A) and replicative domains of the polyprotein 2BC and P3, with the cleavage mediated by proteinase-like activity of the 2A region itself (Ryan et al., J. Gen. Virol. 72:2727-2732, 1991); Vakharia et al., J. Virol. 61:3199-3207, 1987). Similar domains have also been characterized from aphthoviridea and cardioviridae of the picornavirus family (Donnelly et al., J. Gen. Virol. 78:13-21, 1997).

A "self-processing cleavage site" or "self-processing cleavage sequence" as defined above refers to a DNA or amino acid sequence, wherein upon translation, rapid intramolecular (cis) cleavage of a polypeptide comprising the self-processing cleavage site occurs to result in expression of discrete mature protein or polypeptide products. Such a "self-processing cleavage site", may also be referred to as a post-translational or co-translational processing cleavage site, exemplified herein by a 2A site, sequence or domain. It has been reported that a 2A site, sequence or domain demonstrates a translational effect by modifying the activity of the ribosome to promote hydrolysis of an ester linkage, thereby releasing the polypeptide from the translational complex in a manner that allows the synthesis of a discrete downstream translation product to proceed (Donnelly, 2001). Alternatively, a 2A site, sequence or domain demonstrates "auto-proteolysis" or "cleavage" by cleaving its own C-terminus in cis to produce primary cleavage products (Furler; Palmenberg, Ann. Rev. Microbiol. 44:603-623 (1990)).

Although the mechanism is not part of the invention, the activity of a 2A-like sequence may involve ribosomal skipping between codons which prevents formation of peptide bonds (de Felipe et al., Human Gene Therapy 11:1921-1931 (2000); Donnelly et al., J. Gen. Virol. 82:1013-1025 (2001)), although it has been considered that the domain acts more like an autolytic enzyme (Ryan et al., Virol. 173:35-45 (1989). Studies in which the Foot and Mouth Disease Virus (FMDV) 2A coding region was cloned into expression vectors and transfected into target cells showed FMDV 2A cleavage of artificial reporter polyproteins in wheat-germ lysate and transgenic tobacco plants (Halpin et al., U.S. Ser. No. 5,846, 767; 1998 and Halpin et al., The Plant Journal 17:453-459, 1999); Hs 683 human glioma cell line (de Felipe et al., Gene Therapy 6:198-208, 1999); hereinafter referred to as "de Felipe II"); rabbit reticulocyte lysate and human HTK-143 cells (Ryan et al., EMBO J. 13:928-933 (1994)); and insect cells (Roosien et al., J. Gen. Virol. 71:1703-1711, 1990). The FMDV 2A-mediated cleavage of a heterologous polyprotein has been shown for IL-12 (p40/p35 heterodimer; Chaplin et al., J. Interferon Cytokine Res. 19:235-241, 1999). The reference demonstrates that in transfected COS-7 cells, FMDV 2A mediated the cleavage of a p40-2A-p35 polyprotein into biologically functional subunits p40 and p35 having activities associated with IL-12.

The FMDV 2A sequence has been incorporated into retroviral vectors, alone or combined with different IRES sequences to construct bicistronic, tricistronic and tetracistronic vectors. The efficiency of 2A-mediated gene expression in animals was demonstrated by Furler (2001) using recombinant adeno-associated viral (AAV) vectors encoding a-synuclein and EGFP or Cu/Zn superoxide dismutase (SOD-1) and EGFP linked via the FMDV 2A sequence. EGFP and α-synuclein were expressed at substantially higher levels from vectors which included a 2A sequence relative to corresponding IRES-based vectors, while SOD-1 was expressed at comparable or slightly higher levels. Furler also demonstrated that the 2A sequence results in bicistronic gene expression in vivo after injection of 2A-containing AAV vectors into rat substantia nigra.

For the present invention, the DNA sequence encoding a self-processing cleavage site is exemplified by viral sequences derived from a picornavirus, including but not limited to an entero-, rhino-, cardio-, aphtho- or Foot-and-Mouth Disease Virus (FMDV). In one preferred embodiment, the self-processing cleavage site coding sequence is derived from a FMDV. Self-processing cleavage sites include but are not limited to 2A and 2A-like sites, sequences or domains (Donnelly et al., J. Gen. Virol. 82:1027-1041 (2001). Positional subcloning of a 2A sequence between two or more heterologous DNA sequences in a vector construct allows the delivery and expression of two or more open reading frames by operable linkage to a single promoter. Preferably, self-processing cleavage sites such as FMDV 2A sequences provide a unique means to express and deliver from a single viral vector, two or more proteins, polypeptides or peptides which can be individual parts of, for example, an immunoglobulin Factor VIII, a cytokine, or another heterodimeric protein, an antibody, or a heterodimeric receptor.

FMDV 2A is a polyprotein region that functions in the FMDV genome to direct a single cleavage at its own C-terminus, thus functioning in cis. The FMDV 2A domain is typically reported to be about nineteen amino acids in length ((LLNFDLLKLAGDVESNPGP (SEQ ID NO: 1); TLNFDLLKLAGDVESNPGP (SEQ ID NO: 2); Ryan et al., J. Gen. Virol. 72:2727-2732 (1991)), however oligopeptides of as few as fourteen amino acid residues ((LLKLAGDVESNPGP (SEQ ID NO: 3)) have also been shown to mediate cleavage at the 2A C-terminus in a fashion similar to its role in the native FMDV polyprotein processing.

Variations of the 2A sequence have been studied for their ability to mediate efficient processing of polyproteins (Donnelly MLL et al. 2001). Homologues and variant 2A sequences are included within the scope of the invention and include but are not limited to the sequences presented in Table 1, below:

TABLE 1

Table of Exemplary 2A Sequences

| (SEQ ID) | SEQUENCE |
|---|---|
| NO: 1 | LLNFDLLKLAGDVESNPGP |
| NO: 2 | TLNFDLLKLAGDVESNPGP |
| NO: 3 | LLKLAGDVESNPGP |
| NO: 4 | NFDLLKLAGDVESNPGP |
| NO: 5 | QLLNFDLLKLAGDVESNPGP |
| NO: 6 | APVKQTLNFDLLKLAGDVESNPGP |
| NO: 7 | VTELLYRMKRAETYCPRPLLAIHPTEARHKQKIVAPVKQTLNFDLLKLAGDVESNPGP |
| NO: 8 | LLAIHPTEARHKQKIVAPVKQTLNFDLLKLAGDVESNPGP |
| NO: 9 | EARHKQKIVAPVKQTLNFDLLKLAGDVESNPGP |

Distinct advantages of self-processing cleavage sequences, such as a 2A sequence or a variant thereof are their use in generating vectors expressing self-processing polyproteins. This invention includes lentivectors which comprise the coding sequence for two or more proteins or polypeptides linked via self-processing cleavage sites such that the individual proteins or polypeptides are expressed in equimolar or close to equimolar amounts following the cleavage of the polyprotein due to the presence of the self-processing cleavage site. These proteins may be heterologous to the vector itself, to each other or to the self-processing cleavage site, e.g., FMDV. Thus the self-processing cleavage sites for use in practicing the invention do not discriminate between heterologous proteins or polypeptides and coding sequences derived from the same source as the self-processing cleavage site, in the ability to function or mediate cleavage.

The expression levels of individual proteins, polypeptides or peptides from a promoter driving a single open reading frame comprising more than two coding sequences are closer to equimolar as compared to expression levels achievable using IRES sequences or dual promoters. Elimination of dual promoters reduces promoter interference that may result in reduced and/or impaired levels of expression for each coding sequence.

In one preferred embodiment, the FMDV 2A sequence included in a lentivector according to the invention encodes amino acid residues comprising LLNFDLLKLAGDVESNPGP (SEQ ID NO: 1). Alternatively, a lentivector according to the invention may encode amino acid residues for other 2A-like regions as discussed in Donnelly et al., J. Gen. Virol. 82:1027-1041 (2001) and including but not limited to a 2A-like domain from picornavirus, insect virus, Type C rotavirus, trypanosome repeated sequences or the bacterium, Thermatoga maritima.

The invention contemplates the use of nucleic acid sequence variants that encode a self-processing cleavage site, such as a 2A or 2A-like polypeptide, and nucleic acid coding sequences that have a different codon for one or more of the amino acids relative to that of the parent (native) nucleotide. Such variants are specifically contemplated and encompassed by the present invention. Sequence variants of self-processing cleavage peptides and polypeptides are included within the scope of the invention as well.

Optimal alignment of sequences for comparison can be conducted, e.g., by the local homology algorithm of Smith &

Waterman, Adv. Appl. Math. 2: 482 (1981), by the homology alignment algorithm of Needleman & Wunsch, J Mol. Biol. 48: 443 (1970), by the search for similarity method of Pearson & Lipman, Proc. Nat'l. Acad. Sci. USA 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), by the BLAST algorithm, Altschul et al., J Mol. Biol. 215: 403-410 (1990), with software that is publicly available through the National Center for Biotechnology Information (http://www.ncbi.nlm.nih.gov/), or by visual inspection (see generally, Ausubel et al., infra). For purposes of the present invention, optimal alignment of sequences for comparison is most preferably conducted by the local homology algorithm of Smith & Waterman, Adv. Appl. Math. 2: 482 (1981). See, also, Altschul, S. F. et al., 1990 and Altschul, S. F. et al., 1997.

In accordance with the present invention, also encompassed are sequence variants which encode self-processing cleavage polypeptides and polypeptides themselves that have 80, 85, 88, 89, 90, 91, 92, 93, 94, 95, 96, 97, 98, 99% or more sequence identity to the native sequence.

A nucleic acid sequence is considered to be "selectively hybridizable" to a reference nucleic acid sequence if the two sequences specifically hybridize to one another under moderate to high stringency hybridization and wash conditions. Hybridization conditions are based on the melting temperature (Tm) of the nucleic acid binding complex or probe. For example, "maximum stringency" typically occurs at about Tm-5° C. (5° below the Tm of the probe); "high stringency" at about 5-10° below the Tm; "intermediate stringency" at about 10-20° below the Tm of the probe; and "low stringency" at about 20-25° below the Tm. Functionally, maximum stringency conditions may be used to identify sequences having strict identity or near-strict identity with the hybridization probe; while high stringency conditions are used to identify sequences having about 80% or more sequence identity with the probe.

Moderate and high stringency hybridization conditions are well known in the art (see, for example, Sambrook, et al, 1989, Chapters 9 and 11, and in Ausubel, F. M., et al., 1993. An example of high stringency conditions includes hybridization at about 42° C. in 50% formamide, 5×SSC, 5×Denhardt's solution, 0.5% SDS and 100 µg/ml denatured carrier DNA followed by washing two times in 2×SSC and 0.5% SDS at room temperature and two additional times in 0.1× SSC and 0.5% SDS at 42° C. 2A sequence variants that encode a polypeptide with the same biological activity as the 2A polypeptides described herein and hybridize under moderate to high stringency hybridization conditions are considered to be within the scope of the present invention.

As a result of the degeneracy of the genetic code, a number of coding sequences can be provided which encode the same protein, polypeptide or peptide, such as 2A or a 2A-like peptide. For example, the triplet CGT encodes the amino acid arginine. Arginine is alternatively encoded by CGA, CGC, CGG, AGA, and AGG. Therefore it is appreciated that such substitutions in the coding region fall within the sequence variants that are covered by the present invention.

Removal of Self-Processing Peptide Sequences

One concern associated with the use of self-processing peptides, such as a 2A or 2A-like sequence is that the C terminus of the expressed polypeptide contains amino acids derived from the self-processing peptide, i.e. 2A-derived amino acid residues. These amino acid residues are "foreign" to the host and may elicit an immune response when the recombinant protein is expressed in vivo (i.e., expressed from a viral or non-viral vector in the context of gene therapy or administered as an in vitro-produced recombinant protein or polypeptide) or delivered in vivo following in vitro or ex vivo expression. In addition, if not removed, self-processing peptide-derived amino acid residues may interfere with protein secretion in producer cells and/or alter protein conformation, resulting in a less than optimal expression level and/or reduced biological activity of the recombinant protein.

The invention includes lenti-based expression constructs, engineered such that an additional proteolytic cleavage site is provided between a first protein or polypeptide coding sequence (the first or 5' ORF) and the self processing cleavage site as a means for removal of self processing cleavage site derived amino acid residues that are present in the expressed protein product.

Examples of additional proteolytic cleavage sites are furin cleavage sites with the consensus sequence RXK(R)R (SEQ ID NO: 10), which can be cleaved by endogenous subtilisin-like proteases, such as furin and other serine proteases. The inventors have demonstrated that self-processing 2A amino acid residues at the C terminus of a first expressed protein can be efficiently removed by introducing a furin cleavage site RAKR (SEQ ID NO: 18) between the first polypeptide and a self-processing 2A sequence. In addition, use of a plasmid containing a 2A sequence and a furin cleavage site adjacent to the 2A sequence was shown to result in a higher level of protein expression than a plasmid containing the 2A sequence alone. This improvement provides a further advantage in that when 2A amino acid residues are removed from the C-terminus of the protein, longer 2A- or 2A like sequences or other self-processing sequences can be used. See, e.g., U.S. Patent Publication Nos. 20040265955 and 20050003482, expressly incorporated by reference herein.

It is often advantageous to produce therapeutic proteins, polypeptides, fragments or analogues thereof with fully human characteristics. These reagents avoid the undesired immune responses induced by proteins, polypeptides, fragments or analogues thereof originating from different species. To address possible host immune responses to amino acid residues derived from self-processing peptides, the coding sequence for a proteolytic cleavage site may be inserted (using standard methodology known in the art) between the coding sequence for a first protein and the coding sequence for a self-processing peptide so as to remove the self-processing peptide sequence from the expressed protein or polypeptide. This finds particular utility in therapeutic and diagnostic proteins and polypeptides for use in vivo.

Any additional proteolytic cleavage site known in the art that can be expressed using recombinant DNA technology may be employed in practicing the invention. Exemplary additional proteolytic cleavage sites which can be inserted between a polypeptide or protein coding sequence and a self processing cleavage sequence include, but are not limited to a:

a). Furin consensus sequence or site: RXK(R)R (SEQ ID. NO:10);

b). Factor Xa cleavage sequence or site: IE(D)GR (SEQ ID. NO:11);

c). Signal peptidase I cleavage sequence or site: e.g., LAG-FATVAQA (SEQ ID. NO: 12); and d). Thrombin cleavage sequence or site: LVPRGS (SEQ ID. NO: 13).

As detailed herein, the 2A peptide sequence provides a "cleavage" site that facilitates the generation of both chains of an immunoglobulin or other protein during the translation process. In one exemplary embodiment, the C-terminus of the first protein, for example the immunoglobulin heavy chain, contains approximately 13 amino acid residues that are derived from the 2A sequence itself. The number of residual amino acids is dependent upon the 2A sequence used. As set forth above, when a furin cleavage site sequence, e.g., RAKR (SEQ ID NO: 18), is inserted between the first protein and the 2A sequence, the 2A residues are removed from the C-terminus of the first protein. However, mass spectrum data indicates that the C-terminus of the first protein expressed from the RAKR-2A construct contains two additional amino acid residues, RA, derived from the furin cleavage site RAKR (SEQ ID NO: 18).

In one embodiment, the invention provides a method for removal of these residual amino acids and a composition for expression of the same. A number of novel constructs have been designed that provide for removal of these additional amino acids from the C-terminus of the protein. Furin cleavage occurs at the C-terminus of the cleavage site, which has the consensus sequence RXR(K)R (SEQ ID NO: 19), where X is any amino acid. In one aspect, the invention provides a means for removal of the newly exposed basic amino acid residues R or K from the C-terminus of the protein by use of an enzyme selected from a group of enzymes called carboxypeptidases (CPs), which include, but not limited to, carboxypeptidase D, E and H (CPD, CPE, CPH). Since CPs are able to remove basic amino acid residues at the C-terminus of a protein, all amino acid resides derived from a furin cleavage site which contain exclusively basic amino acids R or K, such as RKKR (SEQ ID NO: 14), RKRR (SEQ ID NO: 15), RRRR (SEQ ID NO: 17), etc, can be removed by a CP. A series of immunoglobulin expression constructs that contain a 2A sequence and a furin cleavage site and which have basic amino acid residues at the C terminus have been constructed to evaluate efficiency of cleavage and residue removal. An exemplary construct design is the following: H chain—furin (e.g, RKKR (SEQ ID NO: 14), RKRR (SEQ ID NO: 15), RRKR (SEQ ID NO: 16) or RRRR (SEQ ID NO: 17))—2A—L chain or L chain—furin (e.g, RKKR (SEQ ID NO: 14), RKRR (SEQ ID NO: 15), RRKR (SEQ ID NO: 16) or RRRR (SEQ ID NO: 17))—2A—H chain A schematic depiction of exemplary constructs is provided in FIGS. 14 and 15, respectively of U.S. Ser. No. 60/659,871, expressly incorporated by reference herein.

As will be apparent to those of skill in the art, there is a basic amino acid residue (K) at the C terminus of the immunoglobulin heavy (H) chain (rendering it subject to cleavage with carboxypeptidase), while the immunoglobulin light (L) chain, terminates with a non-basic amino acid C. In one preferred embodiment of the invention, an antibody expression construct comprising a furin site and a 2A sequence is provided wherein the immunoglobulin L chain is 5' to the immunoglobulin H chain such that following translation, the additional furin amino acid residues are cleaved with carboxypeptidase.

Immunoglobulins and Fragments Thereof

Antibodies are immunoglobulin proteins that are heterodimers of a heavy and light chain and have proven difficult to express in a full-length form from a single vector in mammalian culture expression systems. Three methods are currently used for production of vertebrate antibodies, in vivo immunization of animals to produce "polyclonal" antibodies, in vitro cell culture of B-cell hybridomas to produce monoclonal antibodies (Kohler, et al., Eur. J. Immunol., 6: 511, 1976; Antibodies: A Laboratory Manual, Cold Spring Harbor Laboratory, 1988) and recombinant DNA technology (described for example in Cabilly et al., U.S. Pat. No. 6,331,415).

The basic molecular structure of immunoglobulin polypeptides is known to include two identical light chains with a molecular weight of approximately 23,000 daltons, and two identical heavy chains with a molecular weight 53,000-70,000, where the four chains are joined by disulfide bonds in a "Y" configuration. The amino acid sequence runs from the N-terminal end at the top of the Y to the C-terminal end at the bottom of each chain. At the N-terminal end is a variable region (of approximately 100 amino acids in length) that provides for the specificity of antigen binding.

The present invention provides improved methods for production of immunoglobulins of all types, including, but not limited to full length antibodies and antibody fragments having a native sequence (i.e. that sequence produced in response to stimulation by an antigen), single chain antibodies which combine the antigen binding variable region of both the heavy and light chains in a single stably-folded polypeptide chain; univalent antibodies (which comprise a heavy chain/light chain dimer bound to the Fc region of a second heavy chain); "Fab fragments" which include the full "Y" region of the immunoglobulin molecule, i.e., the branches of the "Y", either the light chain or heavy chain alone, or portions, thereof (i.e., aggregates of one heavy and one light chain, commonly known as Fab'); "hybrid immunoglobulins" which have specificity for two or more different antigens (e.g., quadromas or bispecific antibodies as described for example in U.S. Pat. No. 6,623,940); "composite immunoglobulins" wherein the heavy and light chains mimic those from different species or specificities; and "chimeric antibodies" wherein portions of each of the amino acid sequences of the heavy and light chain are derived from more than one species (i.e., the variable region is derived from one source such as a murine antibody, while the constant region is derived from another, such as a human antibody).

The compositions and methods of the invention find utility in production of immunoglobulins or fragments thereof wherein the heavy or light chain is "mammalian", "chimeric" or modified in a manner to enhance its efficacy. Modified antibodies include both amino acid and nucleic acid sequence variants which retain the same biological activity of the unmodified form and those which are modified such that the activity is altered, i.e., changes in the constant region that improve complement fixation, interaction with membranes, and other effector functions, or changes in the variable region that improve antigen binding characteristics. The compositions and methods of the invention further include catalytic immunoglobulins or fragments thereof.

A "variant" immunoglobulin-encoding polynucleotide sequence may encode a "variant" immunoglobulin amino acid sequence that is altered by one or more amino acids from the reference polypeptide sequence. The variant polynucleotide sequence may encode a variant amino acid sequence that contains "conservative" substitutions, wherein the substituted amino acid has structural or chemical properties similar to the amino acid which it replaces. In addition, or alternatively, the variant polynucleotide sequence may encode a variant amino acid sequence that contains "non-conservative" substitutions, wherein the substituted amino acid has dissimilar structural or chemical properties to the amino acid that it replaces. Variant immunoglobulin-encoding polynucleotides may also encode variant amino acid sequences that contain amino acid insertions or deletions, or both.

The present invention contemplates immunoglobulin sequence variants which encode biologically active immunoglobulins or fragments thereof, wherein the immunoglobulin polypeptide sequence or the nucleotide sequence encoding it has 80, 85, 88, 89, 90, 91, 92, 93, 94, 95, 96, 97, 98, 99% or more sequence identity to the native sequence.

Furthermore, a variant "immunoglobulin-encoding polynucleotide" may encode the same polypeptide as the reference polynucleotide sequence but, due to the degeneracy of the genetic code, has a polynucleotide sequence altered by one or more bases from the reference polynucleotide sequence. Immunoglobulin sequence variants that encode a polypeptide with the same biological activity as the immunoglobulin polypeptides described herein and hybridize under moderate to high stringency hybridization conditions are considered to be within the scope of the present invention.

The term "fragment," when referring to a recombinant immunoglobulin of the invention means a polypeptide which has an amino acid sequence which is the same as part of but not all of the amino acid sequence of the corresponding full length immunoglobulin protein, which either retains essentially the same biological function or activity as the corresponding full length protein, or retains at least one of the functions or activities of the corresponding full length protein. The fragment preferably includes at least 20-100, 20-150 or 20-200 contiguous amino acid residues of the full-length immunoglobulin.

The potential of antibodies as therapeutic modalities is currently limited by long time frame needed to select clones that produce commercially practical levels of immunoglobulin, the production capacity and excessive cost of the current technology. An improved v expression system for immunoblobulin production would permit the expression and delivery of two or more coding sequences, i.e., immunoglobulins with bi- or multiple-specificities from a single vector. The present invention addresses these limitations and is applicable to any immunoglobulin (i.e. an antibody) or fragment thereof as further detailed herein, including engineered antibodies such as single chain antibodies, full-length antibodies or antibody fragments.

Antibody Production

In one example of the present invention, the coding sequence for a first or second chain of a protein or polypeptide is the coding sequence for the heavy chain or a fragment thereof for any immunoglobulin, e.g., IgG, IgM, IgD, IgE or IgA. Alternatively, the coding sequence for a first or second chain of a protein or polypeptide is the coding sequence for the light chain or a fragment thereof for an IgG, IgM, IgD, IgE or IgA. Genes for whole antibody molecules as well as modified or derived forms thereof, such as fragments, e.g., Fab, single chain Fv(scFv) and F(ab')$_2$ are included within the scope of the invention. The antibodies and fragments can be animal-derived, human-mouse chimeric, humanized, DeImmunized™ or fully human. The antibodies can be bispecific and include but are not limited to diabodies, quadroma, miniantibodies, ScBs antibodies and knobs-into-holes antibodies.

In practicing the invention, the production of an antibody, or variant (analogue) or fragment thereof using recombinant DNA technology can be achieved by culturing a modified recombinant host cell under culture conditions appropriate for the growth of that host cell resulting in expression of the coding sequences. In order to monitor the success of expression, antibody levels with respect to the antigen may be monitored using standard techniques such as ELISA, RIA, Western blot and the like. The antibodies are recovered from the culture supernatant using standard techniques known in the art. Purified forms of these antibodies can, of course, be readily prepared by standard purification techniques, e.g., affinity chromatography via protein A, protein G or protein L columns, or based on binding to the particular antigen, or the particular epitope of the antigen for which specificity is desired. Antibodies can also be purified with conventional chromatography, such as an ion exchange or size exclusion column, in conjunction with other technologies, such as ammonia sulfate precipitation and size-limited membrane filtration. Preferred expression systems are designed to include signal peptides so that the resulting antibodies are secreted into the culture medium or supernatant, allowing for ease of purification, however, intracellular production is also possible.

The production and selection of antigen-specific fully human monoclonal antibodies from mice engineered with human Ig loci, has previously been described (Jakobovits A. et al., Advanced Drug Delivery Reviews Vol. 31, pp: 33-42 (1998); Mendez M, et al., Nature Genetics Vol. 15, pp: 146-156 (1997); Jakobovits A. et al., Current Opinion in Biotechnology Vol. 6, No. 5, pp: 561-566 (1995); Green L, et al., Nature Genetics Vol. 7, No. 1, pp: 13-21(1994).

The production and recovery of the antibodies themselves can be achieved in various ways known in the art (Harlow et al., "Antibodies, A Laboratory Manual", Cold Spring Harbor Lab, 1988).

Protein Coding Sequences

As used herein, a "first protein coding sequence" refers to a heterologous nucleic acid sequence encoding a polypeptide or protein molecule or domain or chain thereof including, but not limited to a chain of an antibody or immunoglobulin molecule or fragment thereof, a cytokine or fragment thereof, a growth factor or fragment thereof, a chain of a Factor VIII molecule, a soluble or membrane-associated receptor or fragment thereof, a viral protein or fragment thereof, an immunogenic protein or fragment thereof, a transcriptional regulator or fragment thereof, a proapoptotic molecule or fragment thereof, a tumor suppressor or fragment thereof, an angiogenesis inhibitor or fragment thereof, etc.

As used herein, a "second protein coding sequence" refers to a heterologous nucleic acid sequence encoding: a polypeptide or protein molecule or domain or chain thereof including, but not limited to a chain of an antibody or immunoglobulin or fragment thereof, a cytokine or fragment thereof, a growth factor or fragment thereof, a chain of a Factor VIII molecule, a soluble or membrane-associated receptor or fragment thereof, a viral protein or fragment thereof, an immunogenic protein or fragment thereof, a transcriptional regulator or fragment thereof, a proapoptotic molecule or fragment thereof, a tumor suppressor or fragment thereof, an angiogenesis inhibitor or fragment thereof, etc.

The lentivector constructs of the invention may comprise two or more transgenes or heterologous coding sequences, e.g., a first protein coding sequence, a second protein coding sequence, a third protein coding sequence, etc. The two or more transgenes may be delivered to a cell using one or more lentivectors. When a single lentivector is employed the two or more transgenes are co-expressed by operative linkage to a single promoter and a self processing cleavage sequence such as 2A. Numerous transgenes may be employed in the practice of the present invention and include, but are not limited to, nucleotide sequences encoding one or more of the proteins indicated below or a fragment thereof:

1. A sequence encoding HIF-1α and HIFβ (HIF), p35 and p40 (IL-12), chain A and chain B of insulin, integrins such as, but not limited to alpha V beta 3 or alpha V beta 5, antibody heavy and light chains and the heavy and light chain of Factor VIII.

2. A sequence encoding a soluble receptor, include but are not limited to, the TNF p55 and p75 receptor, the IL-2 receptor, the FGF receptors, the VEGF receptors, TIE2, the IL-6 receptor and the IL-1 receptor;

3. A sequence encoding a cytokine including, but not limited to, any known or later discovered cytokine, for example, IL-1, IL-2, IL-3, IL-4, IL-5, IL-6, IL-7, IL-8, IL-9, IL-10, IL-11, IL-12, IL-13, IL-18, IL-24, INF-α, INF-β, INF-γ, GM-CSF, G-CSF and erythropoietin.

4. A sequence encoding a growth factor including, but not limited to, VEGF, FGF, Angiopoietin-1 and 2, PDGF, EGF, IGF, NGF, IDF, HGF, TGF-α, TGF-beta.

5. A sequence encoding a pro-apoptotic factor including, but not limited to, Bad, Bak, Bax, Bcl2, Bcl-Xs, Bik, Caspases, FasL, and TRAIL.

6. A sequence encoding a tumor suppressor protein or cell cycle regulator including, but not limited to, p53, p16, p19, -21, p27, PTEN, RB1.

7. A sequence encoding an angiogenesis regulator including, but not limited to, angiostatin, endostatin, TIMPs, anti-thrombin, platelet factor 4 (PF4), soluble forms of VEGFR1 (domains 1-7) and VEGFR2 (domains 1-7) fused to an Fc segment of IgG1, VEGF-TRAP, PEDF, PEX, troponin I, thrombospondin, tumstatin, 16 Kd Prolactin.

Cloned sequences and full-length nucleotides encoding any of the above-referenced biologically active molecules may be obtained by well-known methods in the art (Sambrook et al., 1989). In general, the nucleic acid coding sequences are known and may be obtained from public databases and/or scientific publications.

Homologues and variants of heterologous protein and polypeptide coding sequences are included within the scope of the invention based on "sequence identity" or "% homology" to known nucleic acid sequences which are available in public databases and/or selective hybridization under stringent conditions to such known nucleic acid sequences (as described above for self processing cleavage sequences). Homologues and variants of heterologous protein and polypeptide amino acid sequences and nucleic acid sequences that encode them are further included within the scope of the invention. Such sequences may be identified based on "sequence identity" to known sequences using publicly available databases and sequence alignment programs, as described above for self-processing cleavage sequences.

The present invention contemplates heterologous protein and polypeptide variants which encode biologically active proteins, polypeptides or fragments thereof, wherein the protein or polypeptide sequence or the nucleotide sequence encoding it has 80, 85, 88, 89, 90, 91, 92, 93, 94, 95, 96, 97, 98, 99% or more sequence identity to the native sequence.

Furthermore, a variant "heterologous protein or polypeptide-encoding polynucleotide" may encode the same polypeptide as the reference polynucleotide sequence but, due to the degeneracy of the genetic code, has a polynucleotide sequence altered by one or more bases from the reference polynucleotide sequence. Heterologous protein and polypeptide sequence variants that encode a polypeptide with the same biological activity as heterologous protein or polypeptide described herein and hybridize under moderate to high stringency hybridization conditions are considered to be within the scope of the present invention.

Furthermore, a variant "immunoglobulin-encoding polynucleotide" may encode the same polypeptide as the reference polynucleotide sequence but, due to the degeneracy of the genetic code, has a polynucleotide sequence altered by one or more bases from the reference polynucleotide sequence. Immunoglobulin sequence variants that encode a polypeptide with the same biological activity as the immunoglobulin polypeptides described herein and hybridize under moderate to high stringency hybridization conditions are considered to be within the scope of the present invention.

Protein Expression

It will be understood that the lentivectors of the invention find utility in the expression of recombinant proteins and polypeptides in any lentiviral-based protein expression system, a number of which are known in the art and examples of which are described herein.

Following expression, recombinant proteins are recovered from the culture using standard techniques known in the art. The production and recovery of recombinant proteins themselves can be achieved in various ways numerous examples of which are known in the art. For example, the production of a recombinant protein, polypeptide, an analogue or fragment thereof, can be undertaken by culturing the modified recombinant host cells under culture conditions appropriate that host cell resulting in expression of the coding sequence(s). In order to monitor the success of expression, recombinant protein or polypeptide levels are monitored using standard techniques such as ELISA, RIA, Western blot and the like.

Purified forms of the recombinant proteins can, of course, be readily prepared by standard purification techniques known in the art, e.g., affinity chromatography. Recombinant proteins can also be purified using conventional chromatography, such as an ion exchange or size exclusion column, in conjunction with other technologies, such as size-limited membrane filtration. The expression systems are preferably designed to include signal peptides so that the resulting recombinant proteins are secreted into the medium, however, intracellular production is also possible.

The operability of the present invention has been demonstrated by expression of immunoglobulin heavy and light chains using the self-processing cleavage sequence-containing lentivectors of the present invention (See, e.g., Example 2). The advantages associated with use of self-processing cleavage sequences are enhanced by inclusion of an additional proteolytic cleavage site between the coding sequence for a first protein or polypeptide and the self-processing cleavage sequence in the vectors of the invention, resulting in removal of amino acid residues associated with the self-processing cleavage sequence. Efficient removal of 2A residues by incorporation of a furin cleavage site in the vectors of the invention is demonstrated U.S. Patent Publication Nos. 20040265955 and 20050003482.

Vectors for Use in Practicing the Invention

Retroviral vectors are also a common tool for gene delivery (Miller, Nature 357: 455-460, 1992). Retroviral vectors and more particularly lentiviral vectors may be used in practicing the present invention. Accordingly, the term "retrovirus" or "retroviral vector", as used herein is meant to include "lentivirus" and "lentiviral vectors" respectively. Retroviral vectors have been tested and found to be suitable delivery vehicles for the stable introduction of genes of interest into the genome of a broad range of target cells. The ability of retroviral vectors to deliver unrearranged, single copy transgenes into cells makes retroviral vectors well suited for transferring genes into cells. Further, retroviruses enter host cells by the binding of retroviral envelope glycoproteins to specific cell surface receptors on the host cells. Consequently, pseudotyped retroviral vectors in which the encoded native envelope protein is replaced by a heterologous envelope protein that has a different cellular specificity than the native envelope protein (e.g., binds to a different cell-surface receptor as compared to the native envelope protein) may also find utility in practicing the present invention. The ability to direct the delivery of retroviral vectors encoding one or more target protein coding sequences to specific target cells is desirable in practice of the present invention.

The invention relates to retroviral vectors, producer cells, and producer cell lines. In particular, the invention relates to a novel approach for the expression of multimeric, heterologous coding sequences in a single mammalian cell using one or more self-inactivating ("SIN") retroviral vectors that encode a heterologous sequence. More particularly, the retroviral vectors are SIN lentiviral vectors. The invention further relates to methods of using SIN lentiviral vectors for making multimeric recombinant proteins.

The present invention provides retroviral vectors that include e.g., retroviral transfer vectors comprising one or more transgene sequences and retroviral packaging vectors comprising one or more packaging elements. In particular, the present invention provides pseudotyped retroviral vectors encoding a heterologous or functionally modified envelope protein for producing pseudotyped retrovirus. Preferably, the heterologous env gene comprises a VSV-G or baculoviral gp64 env gene, although those skilled in the art will appreciate that other env genes may be employed.

One preferred method of vector production is transient transfection of plasmids containing the viral packaging genes and the transgene into a cell line. Alternatively, the vectors are produced via transfection, transduction or infection into a packaging cell line to make producer cells. Methods for transfection, transduction or infection are well known by those of skill in the art. Both transiently transfected and producer cells are effective to generate viral particles that contain the transgene. For either the stable or transient production method the recombinant virus is recovered from the culture media, concentrated and/or purified, and titrated by standard methods used by those of skill in the art.

The core sequence of the retroviral vectors of the present invention may be readily derived from a wide variety of retroviruses, including for example, B, C, and D type retroviruses as well as spumaviruses and lentiviruses (RNA Tumor Viruses, Second Edition, Cold Spring Harbor Laboratory, 1985). An example of a retrovirus suitable for use in the compositions and methods of the present invention includes, but is not limited to, a lentivirus. Other retroviruses suitable for use in the compositions and methods of the present invention include, but are not limited to, Avian Leukosis Virus, Bovine Leukemia Virus, Murine Leukemia Virus, Mink-Cell Focus-Inducing Virus, Murine Sarcoma Virus, Reticuloendotheliosis virus and Rous Sarcoma Virus. Preferred Murine Leukemia Viruses include 4070A and 1504A (Hartley and Rowe, J. Virol. 19:19-25, 1976), Abelson (ATCC No. VR-999), Friend (ATCC No. VR-245), Graffi, Gross (ATCC No. VR-590), Kirsten, Harvey Sarcoma Virus and Rauscher (ATCC No. VR-998), and Moloney Murine Leukemia Virus (ATCC No. VR-190). Such retroviruses may be readily obtained from depositories or collections such as the American Type Culture Collection ("ATCC"; Rockville, Md.), or isolated from known sources using commonly available techniques.

Preferably, a retroviral vector sequence of the present invention is derived from a lentivirus. A preferred lentivirus is a human immunodeficiency virus, e.g., type 1 or 2 (i.e., HIV-1 or HIV-2, wherein HIV-1 was formerly called lymphadenopathy associated virus 3 (HTLV-III) and acquired immune deficiency syndrome (AIDS)-related virus (ARV)), or another virus related to HIV-1 or HIV-2 that has been identified and associated with AIDS or AIDS-like disease. Other lentiviruses include a sheep Visna/maedi virus, a feline immunodeficiency virus (FIV), a bovine lentivirus, simian immunodeficiency virus (SIV), an equine infectious anemia virus (EIAV), and a caprine arthritis-encephalitis virus (CAEV).

The various genera and strains of retroviruses suitable for use in the compositions and methods are well known in the art (see, e.g., Fields Virology, Third Edition, edited by B. N. Fields et al., Lippincott-Raven Publishers (1996), see e.g., Chapter 58, Retroviridae: The Viruses and Their Replication, Classification, pages 1768-1771, including Table 1.

The packaging system used to generate retroviral vectors is composed of at least two packaging vectors, a first packaging vector which comprises a first nucleotide sequence comprising a gag, a pol, or gag and pol genes and a second packaging vector which comprises a second nucleotide sequence comprising a heterologous or functionally modified envelope gene. In a preferred embodiment, the retroviral elements are derived from a lentivirus, such as HIV. Preferably, the vectors lack a functional tat gene and/or functional accessory genes (vif vpr, vpu, vpx, nef). In a further preferred embodiment, the system further comprises a third packaging vector that comprises a nucleotide sequence comprising a rev gene. The packaging system can be provided in the form of a packaging cell that contains the first, second, and, optionally, third nucleotide sequences.

The invention is applicable to a variety of systems, and those skilled in the art will appreciate the common elements shared across differing groups of retroviruses. The description herein uses lentiviral systems as a representative example. However, all retroviruses share the features of enveloped virions with surface projections and containing one molecule of linear, positive-sense single stranded RNA, a genome consisting of a dimer, and the common proteins gag, pol and env.

Lentiviruses share several structural virion proteins in common, including the envelope glycoproteins SU (gp120) and TM (gp41), which are encoded by the env gene; CA (p24), MA (p17) and NC (p7-11), which are encoded by the gag gene; and RT, PR and IN encoded by the pol gene. HIV-1 and HIV-2 contain accessory and other proteins involved in regulation of synthesis and processing virus RNA and other replicative functions. The accessory proteins, encoded by the vif, vpr, vpu/vpx, and nef genes, can be omitted (or inactivated) from the recombinant system. In addition, tat and rev can be omitted or inactivated, e.g., by mutation or deletion.

First generation lentiviral vector packaging systems provide separate packaging constructs for gag/pol and env, and typically employ a heterologous or functionally modified envelope protein for safety reasons. See e.g., Miller and Buttimore, Molec. Cell. Biol. 6(8): 2895-2902 (1986). These modifications minimize the homology between the packaging genome and the viral vector so that the ability of the vector to form recombinants is reduced (see e.g., Miller and Rosman, BioTeclniques 7(9):980-990 (1989)).

In second generation lentiviral vector systems, the accessory genes, vif, vpr, vpu and nef, are deleted or inactivated and the packaging functions are divided into two genomes: one genome expresses the gag and pol gene products, and the other genome expresses the env gene product (see e.g., Bosselman et al., Molec. Cell. Biol. 7(5):1797-1806 (1987); Markowitz et al., J. Virol. 62(4):1120-1124 (1988); Danos and Mulligan, Proc. Nat'l. Acad. Sci. (USA) 85:6460-6464 (1988)). This approach eliminates the ability for co-packaging and subsequent transfer of the psi-genome (containing the viral packaging element psi), as well as significantly decreases the frequency of recombination due to the presence of three retroviral genomes in the packaging cell that must undergo recombination to produce RCR. In the event recombinants arise, mutations or deletions within the undesired gene products render recombinants non-functional (see e.g., Danos and Mulligan, supra Danos and Mulligan, supra;

Boselman et al., supra; and Markowitz et al., supra). In addition, the deletion of the 3' LTR on both packaging function constructs further reduces the ability to form functional recombinants.

Third generation lentiviral vector systems are preferred for use in practicing the present invention and include those from which the tat gene has been deleted or otherwise inactivated (e.g., via mutation). Compensation for the regulation of transcription normally provided by tat can be provided by the use of a strong constitutive promoter, such as the human cytomegalovirus immediate early (HCMV-IE) enhancer/promoter. Other promoters/enhancers can be selected based on strength of constitutive promoter activity, specificity for target tissue (e.g., a liver-specific promoter), or other factors relating to desired control over expression, as is understood in the art. For example, in some embodiments, it is desirable to employ an inducible promoter such as tet to achieve controlled expression. The gene encoding rev is preferably provided on a separate expression construct, such that a typical third generation lentiviral vector system will involve four plasmids: one each for gagpol, rev, envelope and the transfer vector. Regardless of the generation of packaging system employed, gag and pol can be provided on a single construct or on separate constructs.

Typically, the packaging vectors are included in a packaging cell, and are introduced into the cell via transfection, transduction or infection. Methods for transfection, transduction or infection are well known by those of skill in the art. A retroviral/lentiviral transfer vector of the present invention can be introduced into a packaging cell line, via transfection, transduction or infection, to generate a producer cell or cell line. The packaging vectors of the present invention can be introduced into human cells or cell lines by standard methods including, e.g., calcium phosphate transfection, lipofection or electroporation. In some embodiments, the packaging vectors are introduced into the cells together with a dominant selectable marker, such as neo, DHFR, Gln synthetase or ADA, followed by selection in the presence of the appropriate drug and isolation of clones. A selectable marker gene can be linked physically to genes encoding by the packaging vector.

Stable cell lines, wherein the packaging functions are configured to be expressed by a suitable packaging cell, are known. For example, see U.S. Pat. No. 5,686,279; and Ory et al., Proc. Natl. Acad. Sci. (1996) 93:11400-11406, which describe packaging cells. Further description of stable cell line production can be found in Dull et al., 1998, J. Virology 72(11):8463-8471; and in Zufferey et al., 1998, J. Virology 72(12):9873-9880.

Zufferey et al., 1997, Nature Biotechnology 15:871-875, teach a lentiviral packaging plasmid wherein sequences 3' of pol including the HIV-1 envelope gene are deleted. The construct contains tat and rev sequences and the 3' LTR is replaced with poly A sequences. The 5' LTR and psi sequences are replaced by another promoter, such as one that is inducible. For example, a CMV promoter or derivative thereof can be used.

Preferred packaging vectors may contain additional changes to the packaging functions to enhance lentiviral protein expression and to enhance safety. For example, all of the HIV sequences upstream of gag can be removed. Also, sequences downstream of the envelope can be removed. Moreover, steps can be taken to modify the vector to enhance the splicing and translation of the RNA.

Optionally, a conditional packaging system is used, such as that described by Dull et al., J. Virology 72(11):8463-8471, 1998. Also preferred is the use of a self-inactivating vector (SIN), which improves the biosafety of the vector by deletion of the HIV-1 long terminal repeat (LTR) as described, for example, by Zufferey et al., 1998, J. Virology 72(12):9873-9880. Inducible vectors can also be used, such as through a tet-inducible LTR.

Any vector for use in practicing the invention will include heterologous control sequences, such as a constitutive promoter, e.g., the cytomegalovirus (CMV) immediate early promoter, the RSV LTR, the MoMLV LTR, and the PGK promoter; tissue or cell type specific promoters including mTTR, TK, HBV, hAAT, regulatable or inducible promoters, enhancers, etc. Preferred promoters include the LSP promoter (Ill et al., Blood Coagul. Fibrinolysis 8S2:23-30, 1997), the EF1-alpha promoter (Kim et al., Gene 91(2):217-23, 1990) and Guo et al., Gene Ther. 3(9):802-10, 1996). Most preferred promoters include the elongation factor 1-alpha (EF1a) promoter, a phosphoglycerate kinase-1 (PGK) promoter, a cytomegalovirus immediate early gene (CMV) promoter, chimeric liver-specific promoters (LSPs), a cytomegalovirus enhancer/chicken beta-actin (CAG) promoter, a tetracycline responsive promoter (TRE), a transthyretin promoter (TTR), a MND promoter, a simian virus 40 (SV40) promoter and a CK6 promoter. Other promoters/enhancers can be selected based on strength of constitutive promoter activity, specificity for target tissue or other factors relating to desired control over expression, as is understood in the art. The sequences of these and numerous additional promoters are known in the art. The relevant sequences may be readily obtained from public databases and incorporated into vectors for use in practicing the present invention.

The invention uses lentiviral vectors, particles, packaging systems and producer cells capable of producing a high titer recombinant lentivirus capable of selectively infecting human and other mammalian cells. In one embodiment, the recombinant lentivirus of the invention has a titer of greater than $5 \times 10^5$ infectious units/ml. Preferably, the recombinant retrovirus has a titer of greater than $1 \times 10^6$ infectious units/ml. Typically, titer is determined by conventional infectivity assay on 293T, HeLa or HUH7 hepatoma cells.

The present invention also contemplates the inclusion of a gene regulation system for the controlled expression of the coding sequence for two or more polypeptides or proteins of interest. Gene regulation systems are useful in the modulated expression of a particular gene or genes. In one exemplary approach, a gene regulation system or switch includes a chimeric transcription factor that has a ligand binding domain, a transcriptional activation domain and a DNA binding domain. The domains may be obtained from virtually any source and may be combined in any of a number of ways to obtain a novel protein. A regulatable gene system also includes a DNA response element that interacts with the chimeric transcription factor. This element is located adjacent to the gene to be regulated.

Exemplary gene regulation systems that may be employed in practicing the present invention include, the Drosophila ecdysone system (Yao et al., Proc. Nat. Acad. Sci., 93:3346 (1996)), the Bombyx ecdysone system (Suhr et al., Proc. Nat. Acad. Sci., 95:7999 (1998)), the Valentis GeneSwitch® synthetic progesterone receptor system which employs RU-486 as the inducer (Osterwalder et al., Proc Natl Acad Sci 98(22): 12596-601 (2001)); the Tet™ & RevTet™ Systems (BD Biosciences Clontech), which employs small molecules, such as tetracycline (Tc) or analogues, e.g. doxycycline, to regulate (turn on or off) transcription of the target (Knott et al., Biotechniques 32(4):796, 798, 800 (2002)); ARIAD Regulation Technology which is based on the use of a small molecule to bring together two intracellular molecules, each of which is linked to either a transcriptional activator or a DNA binding protein. When these components come together, transcription of the gene of interest is activated. Ariad has two major systems: a system based on homodimerization and a system based on heterodimerization (Rivera et al., Nature Med, 2(9): 1028-1032 (1996); Ye et al., Science 283: 88-91 (2000)), either of which may be incorporated into the vectors of the present invention.

Preferred gene regulation systems for use in practicing the present invention are the ARIAD Regulation Technology and the Tet™ & RevTet™ Systems.

Delivery Of Nucleic Acid Constructs Including Protein or Polypeptide Coding Sequences to Cells The vector constructs of the invention comprising nucleic acid sequences encoding heterologous proteins or polypeptides, and a self-processing cleavage site alone or in combination with a sequence encoding an additional proteolytic cleavage site may be introduced into cells in vitro, ex vivo or in vivo for expression of heterologous coding sequences by cells, e.g., somatic cells in vivo, or for the production of recombinant polypeptides by vector-transduced cells, in vitro or in vivo.

The vector constructs of the invention may be introduced into cells in vitro or ex vivo using standard methodology known in the art. Such techniques include transfection using calcium phosphate, microinjection into cultured cells (Capecchi, Cell 22:479-488 (1980)), electroporation (Shigekawa et al., BioTechn., 6:742-751 (1988)), liposome-mediated gene transfer (Mannino et al., BioTechn., 6:682-690 (1988)), lipid-mediated transduction (Felgner et al., Proc. Natl. Acad. Sci. USA 84:7413-7417 (1987)), and nucleic acid delivery using high-velocity microprojectiles (Klein et al., Nature 327:70-73 (1987)).

For in vitro or ex vivo expression, any cell capable of expressing a functional protein may be employed. Numerous examples of cells and cell lines used for protein expression are known in the art. For example, prokaryotic cells and insect cells may be used for expression. In addition, eukaryotic microorganisms, such as yeast may be used. The expression of recombinant proteins in prokaryotic, insect and yeast systems are generally known in the art and may be adapted for protein or polypeptide expression using the compositions and methods of the present invention.

Exemplary host cells useful for expression further include mammalian cells, such as fibroblast cells, cells from non-human mammals such as ovine, porcine, murine and bovine cells, insect cells and the like. Specific examples of mammalian cells include COS cells, VERO cells, HeLa cells, Chinese hamster ovary (CHO) cells, 293 cell, NSO cells, 3T3 fibroblast cells, W138 cells, BHK cells, HEPG2 cells, DUX cells and MDCK cells.

Host cells are cultured in conventional nutrient media, modified as appropriate for inducing promoters, selecting transformants, or amplifying the genes encoding the desired sequences. Mammalian host cells may be cultured in a variety of media. Commercially available media such as Ham's F10 (Sigma), Minimal Essential Medium (MEM), Sigma), RPMI 1640 (Sigma), and Dulbecco's Modified Eagle's Medium (DMEM, Sigma) are typically suitable for culturing host cells. A given medium is generally supplemented as necessary with hormones and/or other growth factors (such as insulin, transferring, or epidermal growth factor), salts (such as sodium chloride, calcium, magnesium, and phosphate), buffers (such as HEPES), nucleosides (such as adenosine and thymidine), antibiotics, trace elements, and glucose or an equivalent energy source. Any other necessary supplements may also be included at appropriate concentrations that would be known to those skilled in the art. The appropriate culture conditions for a particular cell line, such as temperature, pH and the like, are generally known in the art, with suggested culture conditions for culture of numerous cell lines for example in the ATCC Catalogue available on line at "http://www.atcc.org/SearchCatalogs/AllCollections.cfm"

The lentivectors of the invention may also be administered in vivo via various routes (e.g., intradermally, intravenously, intratumorally, into the brain, intraportally, intraperitoneally, intramuscularly, into the bladder etc.), to deliver multiple genes to express two or more proteins or polypeptides in animal models or human subjects. Dependent upon the route of administration, the therapeutic proteins elicit their effect locally (e.g., in brain or bladder) or systemically (other routes of administration). The use of tissue specific promoters 5' to the open reading frame(s) for a protein or polypeptide in the vectors of the invention may be used to effect tissue specific expression of the two or more proteins or polypeptides encoded by the vector.

Various methods that introduce recombinant lentivectors into target cells in vitro, ex vivo or in vivo have been previously described and are well known in the art. For example, in vivo delivery of the recombinant vectors of the invention may be targeted to a wide variety of organ types including, but not limited to brain, liver, blood vessels, muscle, heart, lung and skin. In the case of ex vivo gene transfer, the target cells are removed from the host and genetically modified in the laboratory using recombinant vectors of the present invention and methods well known in the art.

The recombinant vectors of the invention can be administered using conventional modes of administration including but not limited to the modes described above. The recombinant vectors of the invention may be provided in any of a variety of formulations such as liquid solutions and suspensions, microvesicles, liposomes and injectable or infusible solutions. The preferred form depends upon the mode of administration and the therapeutic application. A from appropriate to the route of delivery may be readily determined using knowledge generally available to those of skill in the relevant art.

Current methods of recombinant immunoglobulin production rely on use of: CHO cells, derivatives thereof; NSO cells; PerC.6 cells; and HEK cells. Most currently used methods for recombinant immunoglobulin production are based on use of vector constructs which include an amplifiable gene such as dihydrofolate reductase (DHFR). As a result the process of recombinant protein production requires the steps of: (1) transfection; (2) selection by culture in medium containing a drug such as Neomycin; (3) amplification of the immunoglobulin coding sequence based on the presence of DHFR in the construct and culture in medium containing a near lethal concentration of methotrexate; (4) screening for viable cells; and (5) further step-wise amplification in culture medium containing increasing concentrations of methotrexate; and (6) further screening at each amplification step to identify viable cells.

Using the DHFR system, the genomic copy number of the nucleic acid encoding the immunoglobulin is increased by the selective pressure of exposing cells to methotrexate, a drug that blocks the activity of DHFR, resulting in higher levels of antibody expression. After 2 to 3 weeks of exposure to methotrexate at a near lethal concentration, the majority of cells die, but cells that overproduce DHFR will survive. Multiple rounds of step-wise amplification in methotrexate-containing medium are typically required, which typically takes from 6 to 12 months, to select a clone that produces at least 20 pg/c/day (pg per cell per day). Frequently as many as 2000-4000 initial clones are screened in order to select a clone that produces at least 20 pg/c/day.

The protein expression levels of different cell clones obtained from step-wise methotrexate amplification can vary widely. As a consequence, the identification of high-producer cell lines is a tedious and labor-intensive process. Several methods for the isolation of clones exist, the most popular being limiting dilution cloning.

In contrast, the methods of the current invention do not require amplification methotrexate-containing medium and hence multiple rounds of successive culturing and screening are avoided. The efficiency of infection and ability of the lentiviral vector to re-infect cells multiple times allow for the rapid generation of cell lines containing numerous genomic copies of the nucleic acid encoding the antibody 2A fusion protein. As a result, 10-fold to 50-fold fewer clones are needed for screening to select a clone that produces at least 20 pg/c/day, shortening the clonal selection process by as much as about 10 months.

For products, like monoclonal antibodies, cell lines must produce at least 20 pg/cell/day to be suitable candidates for commercial production. The combination of fast growth and high productivity makes a cell line a candidate for commercial production. A further important consideration is the stability of the cell line over extended periods of time and upon scale up.

Some clonal cell lines, such as GS-NS0 have been found to be unstable after long term culture. In addition, the presence of methotrexate in long term culture has been shown to result in undesirable genetic heterogeneity in the cells.

The present invention provides advantages in that: 1) the process does not rely on inclusion of an amplifiable gene such as dihydrofolate reductase (DHFR) in the expression construct or use of an agent such as methotrexate for amplification; 2) the process is less expensive because of the fact that the resulting cell line need not be methotrexate resistant thereby eliminating the need to add exogenous methotrexate to the culture medium and allows for additional cell lines capable of large scale culture to be employed in the methods of the invention; 3) the screening time is significantly reduced because the process requires less steps than current commercial processes. The process only requires transfection and selection in a medium containing a drug such as neomycin. No amplification or subsequent rounds of screening are required; 4) the cell line is preferably transfected or infected multiple times over a short period of time to rapidly increase the genomic copy number of the vector. The number of transfections or infections can vary depending, in part, on the coding sequence of the antibody to be expressed, strength of the selected promoter and parent cell line used for expression. In certain embodiments, at least 3 rounds of transfection or infection ("pings") are employed to get optimal expression of a heterologous coding sequence by way of a lentivirus vector; 5) the time for selection of high producer clones is dramatically reduced from the typical 6-12 months to 1-2 months; and 6) the instability of the producer cell line over extended periods of time and upon scale up is less likely to be a problem due to the absence of methotrexate in the culture medium.

In one preferred embodiment, for immunoglobulin production, clonal cell lines of the invention produce at least 20 pg/cell/day, preferably at least 25, 30, 35, 40, 45 or 50, 60, 70, 80, 90, 100, 125, 150 or 200 pg/cell/day. In another preferred embodiment, the timing for selection of clones that produce at least 20 pg/cell/day is less than 4 months, preferably less than 3 months and more preferably less than 2 months. In yet another preferred embodiment temperature for culture is at least 31° C.

In one preferred embodiment, for immunoglobulin production, clonal cell lines of the invention comprise at least 20, preferably at least 25, 30, 35, 40, 45 or 50, 60, 70, 80, 90, 100 genomic copies of the lentiviral vector comprising the nucleic acid encoding the immunoglobulin 2A construct.

In yet another preferred embodiment, clonal cell lines of the invention produce at least 20 pg/cell/day, preferably at least 25, 30, 35, 40, 45 or 50, 60, 70, 80, 90, 100, 125, 150 or 200 pg/cell/day and comprise at least 20 genomic copies of the lentiviral vector comprising the nucleic acid encoding the immunoglobulin 2A construct.

The many advantages of the invention to be realized in recombinant protein and polypeptide production in vivo include administration of a single vector for long-term and sustained expression of two or more recombinant protein or polypeptide ORFs in patients; in vivo expression of two or more recombinant protein or polypeptide ORFs having biological activity; and the natural posttranslational modifications of the recombinant protein or polypeptide generated in human cells.

One preferred aspect is use of the recombinant vector constructs of the present invention for the in vitro production of recombinant proteins and polypeptides. Methods for recombinant protein production are well known in the art and self processing cleavage site-containing vector constructs of the present invention may be utilized for expression of recombinant proteins and polypeptides using such standard methodology.

In one exemplary aspect of the invention, lentivector introduction or administration to a cell is carried out by:

1) introduction or administration of the lentivector to a cell by more than one round of transfection/transduction or infection;

2) culturing the infected cell under conditions that select for a cell expressing the recombinant protein or polypeptide e.g., in medium containing a selection agent such as Neomycin;

3) evaluating expression of the recombinant protein or polypeptide; and 4) collecting the recombinant protein or polypeptide.

In a preferred embodiment the cells are transfected or infected at least 3 times, more preferably at least 4 or 5 times.

Methods and Compositions of the Invention

The invention relates to engineered lentiviral vectors for expression of two or more domains or chains of a multimeric protein. In one aspect the multimeric protein is an immunoglobulin and full-length antibody heavy and light chain coding sequences are expressed using a lentivector comprising a single open reading frame driven by a single promoter wherein the vector comprises a self-processing cleavage site or sequence between the heavy and light chain coding sequences. In another aspect the protein is a multimeric heterologous protein and the full-length coding sequences are expressed using a lentivector comprising a single open reading frame driven by a single promoter wherein the vector comprises one or more self-processing cleavage sites or sequences.

In yet another aspect, the invention provides a method for high level expression of recombinant protein using more than one engineered lentivector, wherein each lentivector encodes a single open reading frame of a multimeric protein driven by a single promoter. For example, for expression of a full-length antibody, individual lentivectors that encode the full-length antibody heavy and light chain, respectively, are used to infect the same cell such that high-level expression of a biologically active antibody results.

In one preferred embodiment, individual populations of host cells are transduced with lentiviral transfer vectors wherein the heterologous protein coding sequence encoded by the vectors is not the same and wherein each lentivector comprises the coding sequence for a single domain or chain of a heterologous protein operably linked to an expression control sequence. For example, a population of cells is transformed with a transfer vector comprising a heterologous protein coding sequence, such as an immunoglobulin light chain coding sequence operably linked to an expression control sequence, and this population or clones derived from it are transduced with a second transfer vector comprising a second heterologous protein coding sequence, such as an immunoglobulin heavy chain coding sequence operably linked to an expression control sequence. The resulting population is cultured under conditions suitable for production of the multimeric protein.

In another preferred embodiment, the transfer vectors further comprise first a strong promoter (e.g. CMV, SV40, MND, or CAG), followed by the antibody heavy chain sequence (H), a furin cleavage site (F), a 2A self-processing sequence derived from the Foot-and-Mouth Disease virus (2A), and an antibody light chain sequence (L). The resulting construct is designated H-F-2A-L. The 2A peptide sequence provides a "cleavage" site that facilitates the generation of two polypeptide chains of the antibody molecule during the translation process as shown in FIG. 1. The furin cleavage site provides a secondary cleavage during antibody secretion pathway to remove 2A residues that are attached to the C terminus of the first gene (i.e. heavy chain in this construct). In yet another preferred embodiment, the transfer vectors further comprise first a strong promoter, followed by the antibody light chain sequence (L), a furin cleavage site (F), a 2A self-processing sequence derived from the Foot-and-Mouth Disease virus (2A), and an antibody heavy chain sequence (H). The resulting construct is designated L-F-2A-H.

Recombinant lentiviral particles were generated and used to transduce human or hamster cells in vitro. ELISA assays for antibody expression from these supernatants revealed that the antibody was produced at high levels in both 293 and CHO cells transduced with CAG H-F-2A-L lentiviral particles. The ratio of the heavy and light chains expressed from the H-F-2A-L construct was approximately 1:1, and the final antibody retained full biological activity based on antibody binding and neutralizing assays.

The present invention finds utility in expression of a full-length monoclonal antibody (IgG, IgM, IgD, IgE, IgA) or antibody fragments from mammalian cells transduced with lentiviral vectors as well as expression of any heterodimeric protein. Given the high transduction efficacy and gene expression level, lentiviral vectors are able to rapidly generate stable cells lines that express high levels of recombinant proteins such as antibodies. In one preferred embodiment, the lentiviral vector comprises a self-processing site or sequence.

The objects of the invention have been achieved by a series of experiments, some of which are described by way of the following non-limiting examples.

EXAMPLES

Example 1

Figure 2:
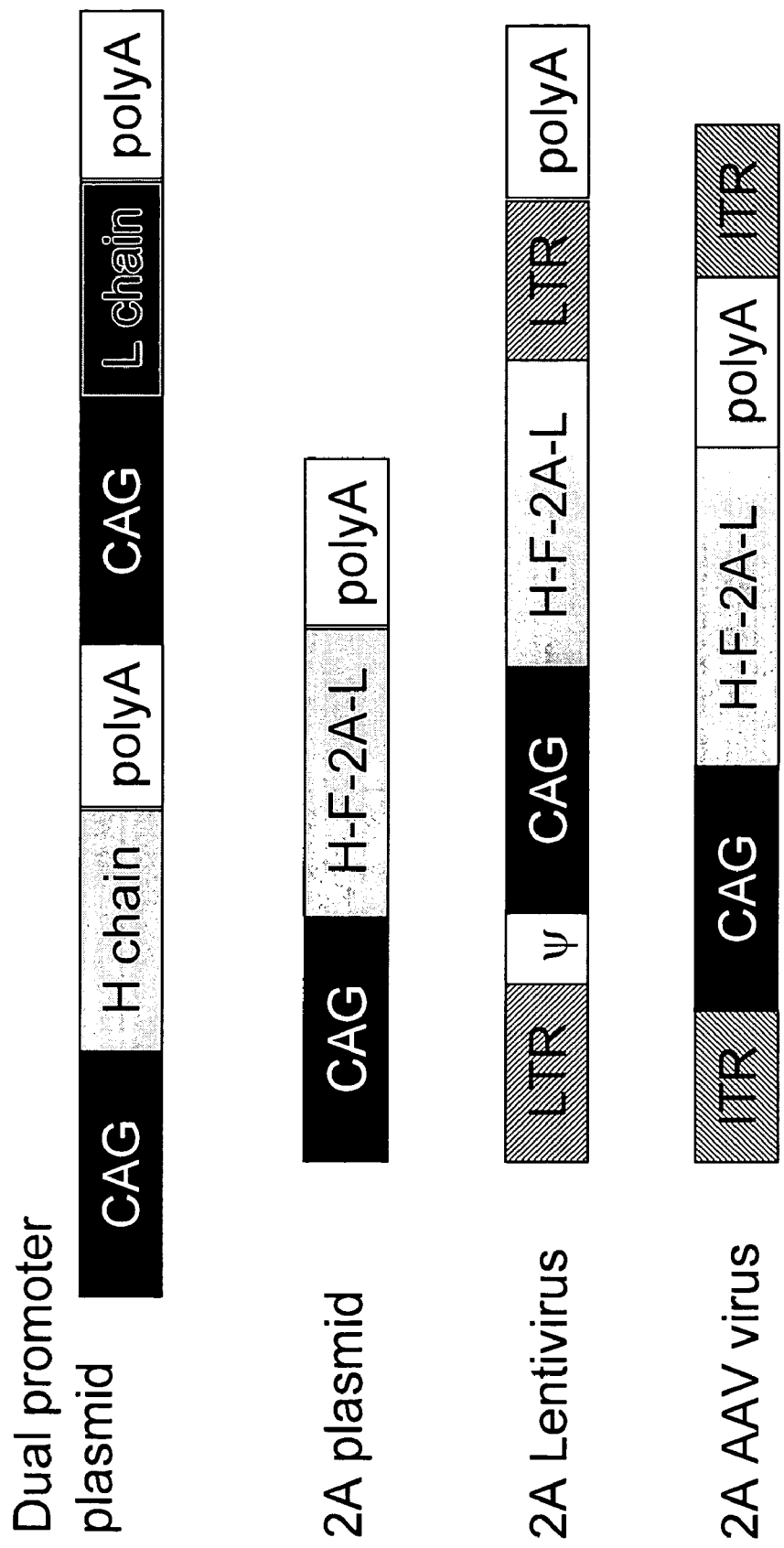
FIG. 2 is a schematic depiction of plasmid, lentivirus and AAV expression cassettes comprising a self-processing cleavage site (2A) for expression of immunoglobulin heavy (H) and light (L) chains operatively linked to a CAG promoter (CAG), wherein the vector may further include an additional proteolytic cleavage site (Furin; "F").

Construction and Production of 2A Antibody Expression Constructs Transfection Plasmids In order to generate lentivector constructs encoding a rat anti-mouse VEGFR2 and human anti-KDR antibody, DNA fragments that encode the antibody heavy chain, furin cleavage site, 2A sequence, and antibody light chain were linked together by PCR extension. A DNA fragment including a furin cleavage site RAKR (SEQ ID NO: 18), and the FMDV 2A sequence APVKQTLNFDLLKLAGDVESNPGP (SEQ ID NO:6), were amplified from a cloned plasmid by PCR. The heavy and light chain fragments were amplified from the cloned plasmids that encode the full-length antibody heavy or light chains respectively. During PCR, an EcoR I restriction endonucleotidase site was added to the 5' prime end of the heavy chain and the 3' prime end of the light chain. The fused heavy chain—furin cleavage site—2A—light chain DNA fragment was digested with EcoR I and purified via agarose gel. The purified DNA fragment was inserted into the pDHFR plasmid at the EcoR I site using T4 DNA ligase. The pDHFR contains a CAG promoter operatively liked to the antibody coding sequences and an SV 40 promoter operatively liked to the DHFR gene. A native signal peptide (leader) was included in the heavy or light chain, respectively, to facilitate secretion of the polypeptides upon synthesis. In addition, the construct also contains a polyA sequence to ensure high-level gene expression (FIG. 2). A pDHFR dual CAG Ab expression plasmid with a CAG promoter that drives the antibody light chain and a second CAG promoter that drives the antibody heavy chain was also constructed (FIG. 2). This plasmid contains the same plasmid backbone as pDHFR but encodes two CAG promoters. A multiple cloning site and a polyA signal sequence follows each CAG promoter sequence. To generate the dual promoter antibody plasmid, an antibody heavy chain or light chain coding sequence was amplified from a cloned plasmid that contains the antibody heavy or light chain sequence, respectively. The antibody light chain sequence was inserted after the first CAG promoter, and the heavy chain after the second CAG promoter using the multiple cloning sites.

Lentiviral Plasmids: The nucleotide coding sequences encoding the KDR and DC101 HF2AL antibodies were cloned into $3^{rd}$ generation lentiviral transfer vectors using standard molecular biology techniques routinely employed by those of skill in the art. The $3^{rd}$ generation lentiviral vector system has previously been described (Dull et al., J. Virol. 72:8463-8471, 1998). Briefly, the transfer vector contains a 5' chimeric RSV/LTR promoter, cPPT (Zennou et al., Cell 101: 173-185, 2000), CAG promoter (Miyazaki et al., Gene 79:269-277, 1989), and SIN LTR (Zufferey et al., J. Virol. 72:9873-9880, 1998). For these studies, the promoter driving the expression of the antibodies is comprised of a CMV enhancer, the chicken beta-actin promoter and splice donor, and the rabbit beta-globin splice acceptor (CAG). A schematic of the lentiviral transfer vector is diagrammed in FIG. 2.

Lentivirus production: Vector production, concentration, p24 analysis, and titer assays were performed as previously described (Dull et al., J. Virol. 72:8463-8471, 1998). Briefly, vectors were prepared by transient transfection in a 10 cm dish with 6.5 ug of pMDLg/pRRE, 2.5 ug of pRSV-Rev, 3.5 ug of pMD2.VSVG-Env, and 10 ug of transfer vector. Vector particles were harvested after 24 hrs, pooled, passed through a 0.2 um cellulose acetate filter, and concentrated by ultracentrifugation for 2 hrs 20 min at 19,500 rpm (50,000 g) in a SW28 swinging bucket rotor. Pellets were resuspended in PBS containing 40 mg/ml lactose and stored in aliquots at −80° C. Detection of the gag p24 protein was evaluated using an Alliance HIV-1 p24 ELISA kit (Perkin Elmer).

AAV production: Recombinant AAV virus was prepared according to standard procedures described in Snyder et al., 1996, In: Current Protocols in Human Genetics, Seidman JS, (editor). John Wiley & Sons: New York; 1-24. Briefly, subconfluent 293 cells were co-transfected with the vector construct pAAV-CAG-KDR (2.13)-HF2AL, AAV helper plasmid pUC-ACG and Adeno helper plasmid pXX6 using the calcium phosphate method. Eight hours after transfection, media was replaced by fresh culture media and cells were incubated for 72 hr, at which point cells were harvested and lysed by three freeze/thaw cycles. Lysates were treated with Benzonase (EM Industries, Hawthorne, N.Y.) for 15 min at 37° C. to digest nucleic acids, and centrifuged to remove the cellular debris. The cleared cell lysate was fractionated by ammonium sulfate precipitation and the rAAV virions were isolated on two sequential CsCl gradients. The gradient fractions containing rAAV were dialyzed against sterile PBS containing $CaCl_2$ and $MgCl_2$, and stored at −80° C. AAV titers were calculated as genomic equivalents, following DNase I and proteinase K treatment, by dot blot and by quantitative PCR as described in Harding et al., 2004 Gene Ther (11): 204-213.

Transfection, selection and cloning: CHOD-cells were seeded at 3×10⁶ in 10 cm plates 24 hr prior to transfection. The transfection of 12 ug of DHFR-containing plasmid per plate was performed with Fugene 6 reagent (Roche Molecular Biochemical) according to the manufacturer's protocol in serum free OPTI-MEM I medium (Invitrogen). 5-6 hours post transfection the medium was replaced with regular growth medium (50:50 F12/DMEM medium supplemented with 2 mM L-glutamine, 10 ug/ml glycine, 15 ug/ml hypoxanthine, 5 ug/ml thymidine and 10% FBS) and incubated at 37° C., 5% $CO_2$. DHFR selection was carried out 48-72 hr post transfection in IMDM medium (JRH) with 2 mM L-glutamine and 10% dialyzed FBS. 10 days post selection clones were picked into 96-well plates, and duplicate plates were made 2-3 days later. 24-hour supernatant was collected from one of the duplicate plates and subjected to ELISA for antibody production and viable cell numbers in each well were determined by CCK-8 proliferation assay (Dojindo). The data from ELISA and CCK-8 assay was used to determine the pg/cell/day antibody production level of each clone. Clones>1 pg/cell/day were expanded from the second plate for further characterization. Clones or populations that were selected for Methotrexate (MTX) amplification were started at 5×10⁵ cells per 10 cm plate in MTX containing medium. MTX concentration was increased from 25 nM to 50 nM, 100 nM, etc. Cells in each selection were passaged 2-3 times before moving into a higher concentration of selective medium and a population of cells was banked (frozen) after each selection.

Lentivirus infection and cloning: CHOD-cells were seeded at 1×10⁵ cells per well in 6-well plates with 2 ml culture medium containing appropriate amount of lentivector and polybrene at 8 ug/ml. Medium was changed 24 hr post infection. Once the cells were confluent they were expanded to a 10 cm plate. Successive rounds of infections were performed at 2-7 day intervals. Populations were subcloned by limiting dilution. Clones were picked and screened as described in the transfection method.

Methods for making clones: In order to determine the relative effectiveness of different vector systems, a comparison of various methods of making cell lines that express a rat anti-mouse VEGFR2 antibody (DC 101) and a human IgG1 anti-KDR antibody (2.13) were evaluated including:

(1) transfection using a plasmid which includes a 2A sequence wherein heavy and light chain are expressed under control of a single promoter, followed by amplification with methotrexate;

(2) transfection using a plasmid which includes dual promoters to express antibody heavy and light chains, followed by amplification with methotrexate;

(3) infection with an AAV construct which includes a 2A sequence wherein heavy and light chains are expressed under control of a single promoter; and (4) infection with a lentivirus construct which includes a 2A sequence wherein heavy and light chains are expressed under control of a single promoter.

Example 2

Comparing Different Methods for Making Stable Antibody-Producing Cell Lines

Stable antibody expressing cell lines were made in CHOD-cells by Fugene 6 transfection with a dual promoter anti-KDR plasmid or a 2A-anti-KDR plasmid as described above. Alternatively, CHOD-cells were infected with either an AAV-2A-anti-KDR vector or a Lenti-2A-anti-KDR vector. In this example CHOD-cells were infected 5 times (5×) at one-week intervals with lenti-2A-KDR vector supernatants containing 500 ng p24. AAV-2A-KDR infections were performed 3 times at an MOI of 10⁵ particles/cell. The transfected populations, lenti 4× and 5× infected populations, and AAV transduced populations were all subcloned. Clones were picked, screened and expanded as described above. Table 2 compares these four methods.

TABLE 2

Evaluation of anti-KDR antibody expressing clones produced by different methods

| Method | Total clones examined | >1 pg/cell/day 96-well | >10 pg/cell/day 6-well | >10 pg/cell/day 10-cm |
|---|---|---|---|---|
| Transfection 2A-KDR | 373 | 2 | 0 | 0 |
| Transfection dual-KDR | 373 | 11 | 0 | 0 |
| AAV-2A-KDR | 800 | 2 | 0 | 0 |
| Lenti-2A-KDR 4x pop | 260 | 260 | >41 | 20 |
| Lenti-2A-KDR 5x pop | 180 | 180 | >14 | 6 |

Figure 3:
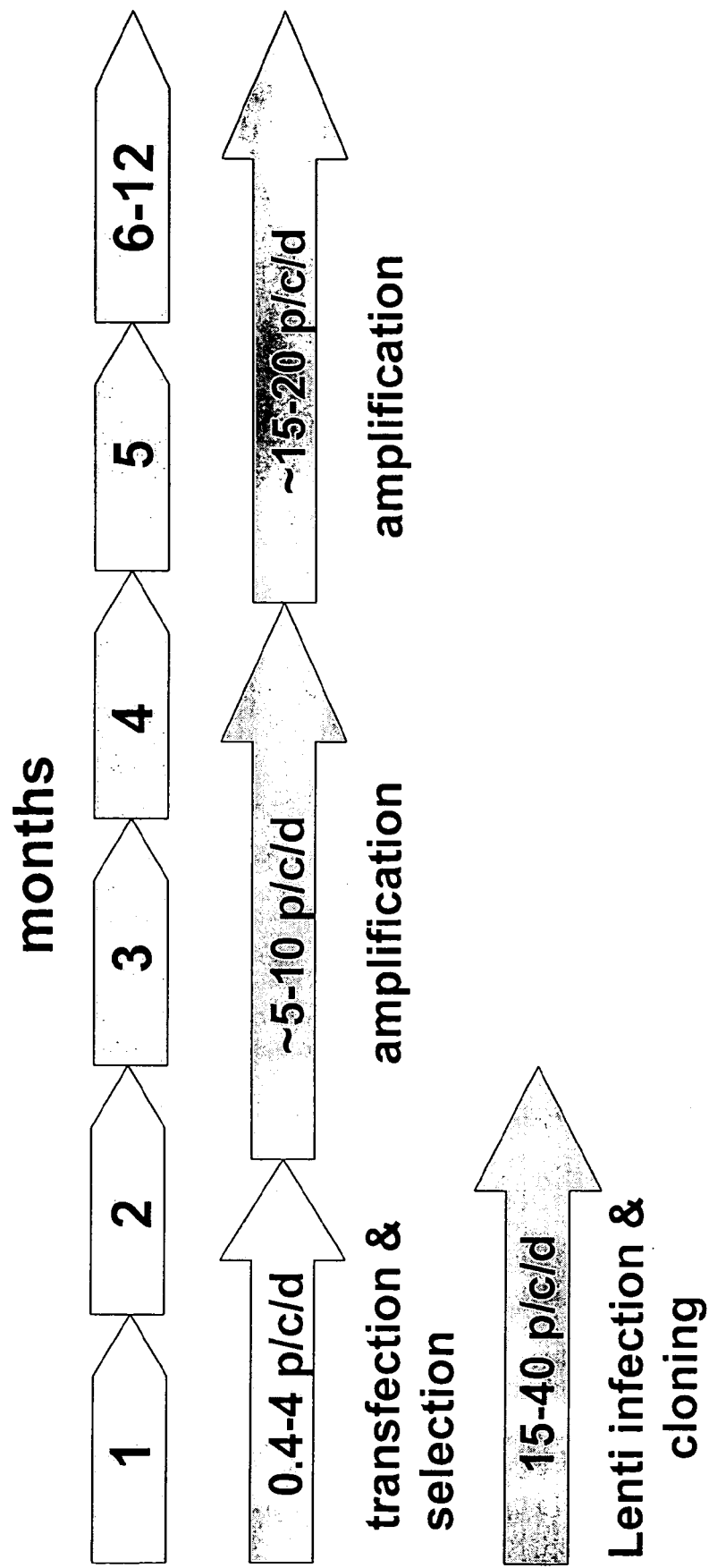
FIG. 3 is a schematic depiction of the time line associated for development of antibody-expressing clones with an illustration of approximate clone development timelines, indicating the advantage of lentivectors over the use of plasmids (transfection and selection) in terms of time and antibody expression level.

The results in Table 3 indicate that transfection of CHOD-cells with a plasmid which comprises an antibody heavy and light chain coding sequence operatively linked to a single promoter and further including a self processing 2A sequence did not show an advantage over dual promoter controlled expression of antibody heavy and light chain coding sequences following transfection and screening. Alternatively, four or five rounds of transfection/transduction of CHOD-cells with lentivector constructs which comprise an antibody heavy and light chain coding sequence operatively linked to a single promoter and further including a self processing 2A sequence resulted in transduction of 100% of clones, yielding higher numbers of clones with significantly greater levels of antibody production compared to the other methods. This approach also reduced the number of clones necessary to screen and significantly reduced the time necessary for isolation of high expressing clones (FIG. 3). Multiple rounds of transduction with a lentivector also increased the copy number in a producer cell resulting in high level protein expression. The twelve lenti clones with the highest expression levels were plated at 1×10⁷ cells/10 cm plate and evaluated for antibody expression at 31° C. (Table 3). These data show that all of the individual clones evaluated express high levels of antibody.

TABLE 3

Lenti-2A-KDR CHOD- expressing clones

| clone # | # of infections | pg/cell/day |
|---|---|---|
| 22 | 4X | 18.2 |
| 30 | 4X | 26.2 |
| 61 | 4X | 18.6 |
| 62 | 4X | 15.0 |
| 70 | 4X | 18.2 |
| 87 | 4X | 26.7 |
| 15 | 5X | 20.1 |
| 65 | 5X | 21.9 |
| 66 | 5X | 16.0 |
| 80 | 5X | 10.7 |
| 88 | 5X | 10.9 |
| 89 | 5X | 9.9 |

A similar experiment comparing methods of producing clones was performed using the rat anti mouse DC101 antibody. CHOD-transfections were performed as described above to compare protein expression following transfection with the 2A DC101 plasmid relative to the dual promoter DC101 plasmid. Alternatively, five serial infections of CHOD-cells were performed at 1-week intervals with the lenti-2A-DC101 vector (200 ng p24/infection). In all three cases the clones were isolated and analyzed for antibody expression. Table 4 compares the expression levels of the 2A-DC101 plasmids with the dual promoter (H+L) plasmids. There was no apparent advantage to the 2A construct in transfection experiments. In general, expression levels of the anti-DC101 antibody are higher than the anti-KDR antibody. The antibody expression in the lenti-2A-DC101 population was much higher than the transfected populations. Again, fewer clones had to be screened due to higher antibody expression levels, and the greater frequency of positive clones as compared to the other systems tested. For example, when expanded to 6 well plates all of the lentiviral clones produced greater than 1 p/c/d of antibody. Ten of the highest producing lenti-2A clones from 6-well plates were expanded to 10-cm plates for further analysis (Table 6). While only 8/10 clones exceeded 10 p/c/d, two of the clones, #45 and 51, were exceptionally high producers, again demonstrating that serial rounds of transduction with lenti 2A vectors results in the need to perform screening of fewer clones in order to obtain high expressing clones. This method also eliminates the need for an amplification step, e.g., with DHFR.

TABLE 4

Comparison of antibody expression levels in CHOD- clones transfected with 2A-DC101 or dual promoter DC101 plasmids.

| Plasmid | Population pg/cell/day | Total clones | # clones >1 p/c/d 96-well | # clones >1 p/c/d 6-well |
|---|---|---|---|---|
| H + L DC101 | 1.7 | 400 | 137 | 120/137 |
| 2A-DC101 | 0.55 | 400 | 84 | 75/84 |
| Lenti 5X | 8.17 | 130 | 130 | 60/60 |

TABLE 5

Antibody expression in CHOD- clones infected 5X with Lenti-2A-DC101

| Clone # | p/c/d |
|---|---|
| 8 | 13.69 |
| 22 | 13.77 |
| 31 | 15.78 |
| 38 | 8.49 |
| 39 | 7.57 |
| 45 | 45 |
| 47 | 9.96 |
| 51 | 40 |
| 55 | 14.09 |
| 59 | 11.48 |

Figure 5:
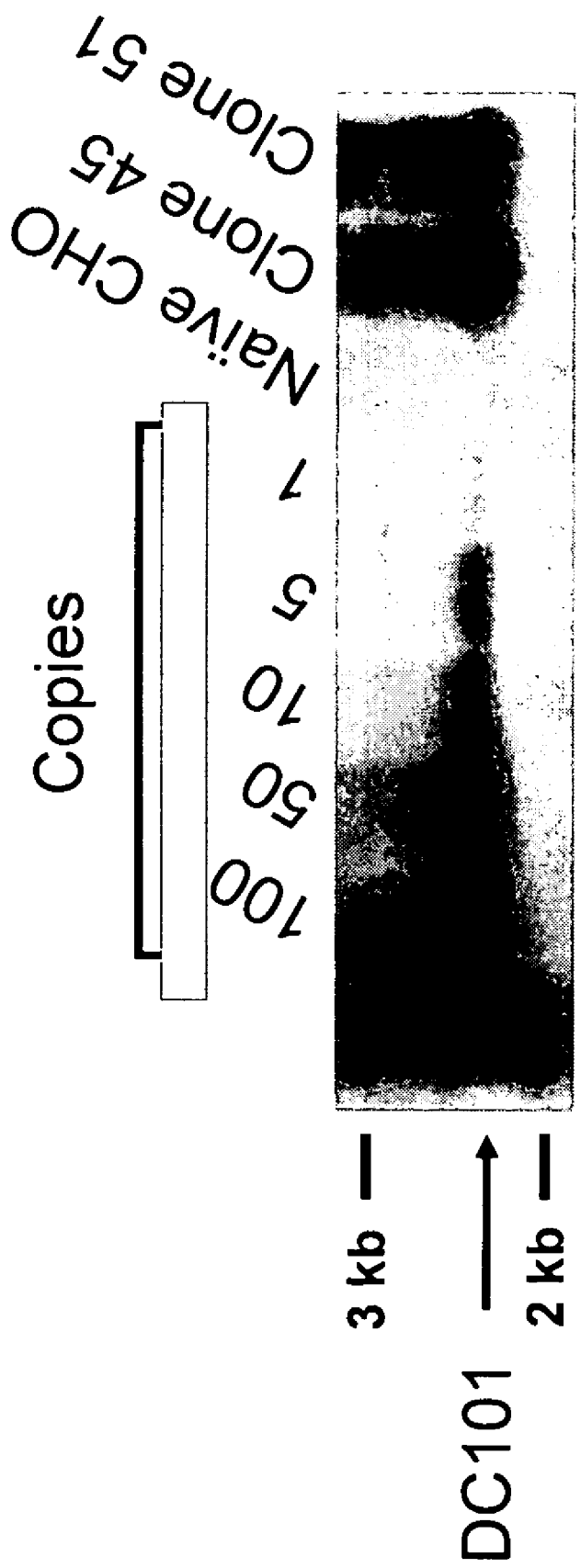
FIG. 5 shows the results of a Southern blot analysis to determine the number of integrated genomic copies of the lentiviral vector for two 5× transfected clones expressing approximately 20-40 pg/cell/day of DC101 antibody. Samples containing known genomic quantities of the lentiviral vector were used as a standard for determining the number of integrated genomic copies.

The number of integrated genomic copies in cells transfected with the lentiviral vector comprising the immunoglobulin 2A construct encoding the DC101 antibody was also examined by Southern Blot analysis (FIG. 5). Genomic DNA was isolated from naive CHO cells and from two 5× transduced clones that express approximately 20-40 pg/cell/day (Clones 45 and 51). The genomic DNA was digested using the restriction enzyme EcoRI using standard conditions and resolved by electrophoresis on a 1% agarose gel in the presence of known, increasing genomic amounts of control DNA to estimate copy number. The resolved DNA fragments were transferred to nylon filter for further analysis. The filter hybridized to a 2.2 Kb radiolabeled DNA fragment comprising the full-length nucleotide sequence encoding the DC101 antibody. The position of the bound probe was visualized using autoradiography and quantitated using a phosphorimager (Molecular Dynamics, Sunnyvale, Calif.).

As shown in FIG. 5, the radiolabeled probe hybridizes to a single 2.2 Kb fragment containing the nucleotide sequence encoding the DC101 antibody. Clones 45 and 51 also exhibit only a single 2.2 Kb band and comprise approximately 33 genomic copies of the lentiviral vector construct. This number is consistent with the Taq-man results presented above. Thus, within a 5-week period, a high producer cell line comprising 33 copies of the antibody coding sequences may be prepared without drug-based amplification.

Figure 6:
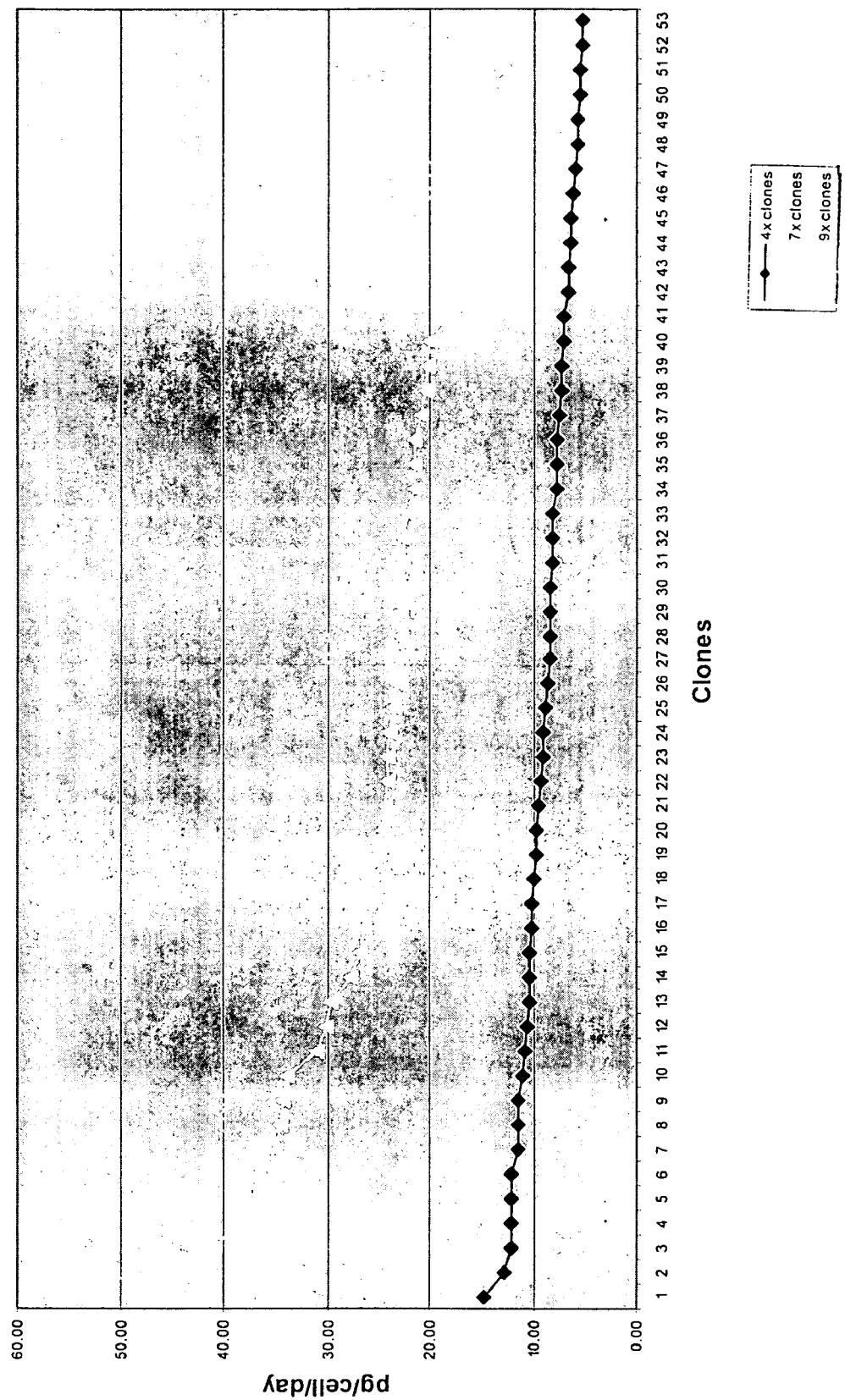
FIG. 6 illustrates the antibody expression levels for 60 individual clones isolated from cells that had been transfected 4×, 7× or 9× with the lentiviral 2A DC101-encoding vector. The amount of antibody produced (in pg/cell/day) is plotted against the number of clones that express that amount of recombinant DC101 antibody from each population.

CHOD-cells were transfected with 200 ng of p24 of the lentiviral vector encoding DC101 4×, 7× or 9× at 3 day intervals. Populations from the transfected cells were subcloned and approximately 100-160 clones were expanded into 96 well plates and the supernatants screened by ELISA to determine DC101 expression levels. Cell number was determined using a CCK8 assay. Approximately 50 high expressing clones were chosen, expanded in 6-well plates and the amount of antibody produced (pg/cell/day) was determined for each clone (FIG. 6). As the number of transfections was increased, there was a concomitant increase in the number of cells that express increasing levels of antibody, e.g., compare pg/cell/day of antibody production for 4× and 9× clones (FIG. 6). Furthermore, approximately 50% of the cells transfected in the 9× population expressed greater that 30 pg/cell/day thereby greatly reducing the time and number of clones required to be screened to identify cell lines capable of expressing commercially-relevant amounts of recombinant antibody.

Example 3

Demonstration of Antibody Expression Levels from Different Cell Types Following Transduction with Lentiviral Constructs Antibody expression levels were evaluated for lenti human anti-KDR and lenti rat anti-VEGFR2 (DC101) while looking at a number of variables: different cell types, different promoters, and different lenti constructs. The different cell types examined were CHOD-cells, PerC6 cells and HuH7 cells. The different promoters were CAG, CMV and MND.

For the assays CHOD-cells, PerC6 cells, or HuH7 cells were seeded at 1×10$^5$ cells per well in 6-well plates containing 2 ml of culture medium including an appropriate amount of lentivector and polybrene at 8 ug/ml. Infection was allowed to proceed as described above. The medium was changed 24 hr post infection. Cells were maintained in 6-well plates until they reached 80% confluence. The medium was then refreshed and at 24 hr and supernatant collected from each well. The cell numbers in each well were determined by hemocytometer. The antibody expression level was determined by ELISA.

Figure 4:
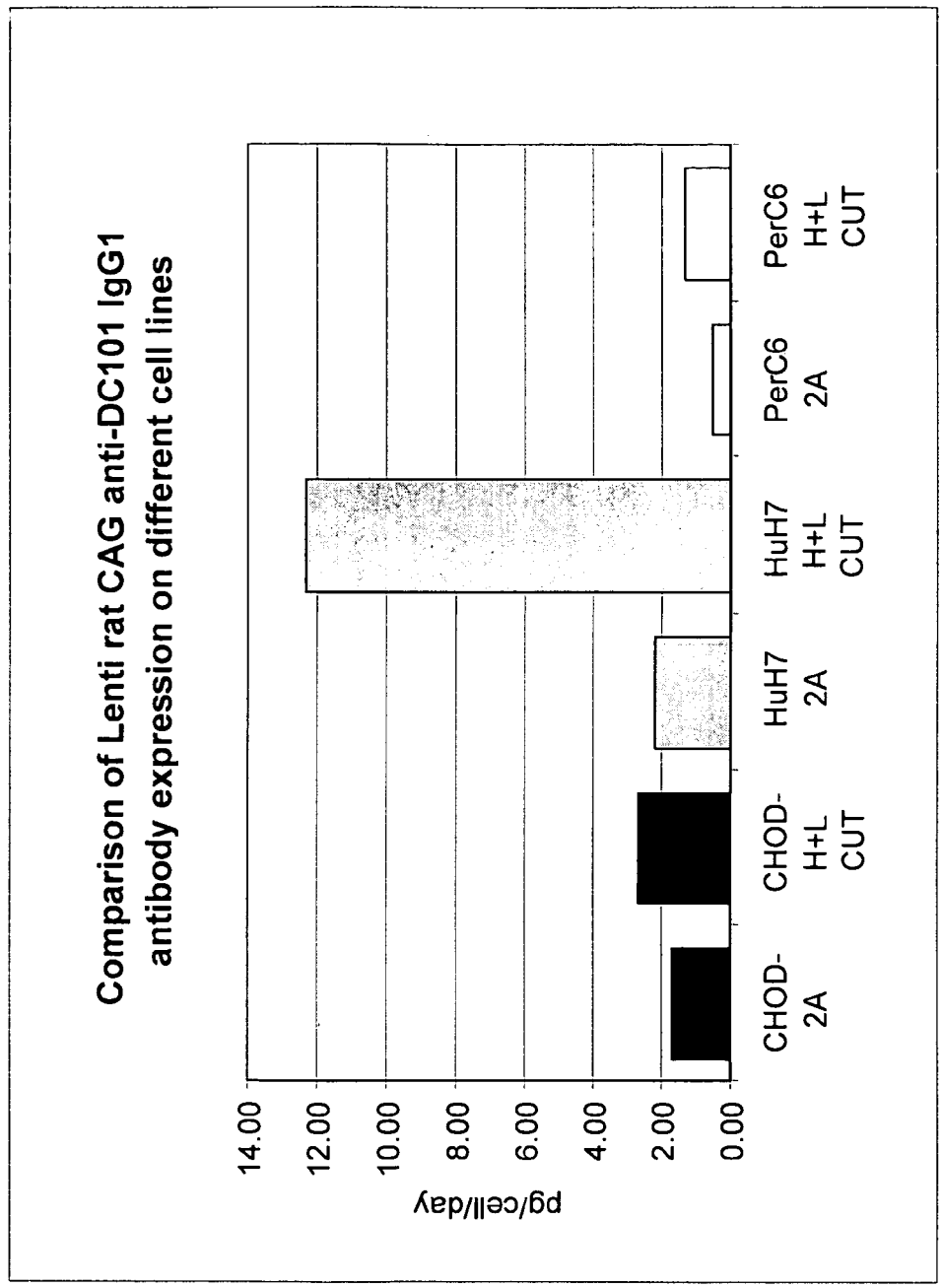
FIG. 4 illustrates the expression of a full length rat anti-VEGFR2 monoclonal antibody (CAG-DC101 IgG1) in different cell lines (CHOD-, HuH7 and PerC6) following transduction with a lentivector, wherein 2A refers to expression of DC101 via a single vector including a self processing sequence.
Figure 7:
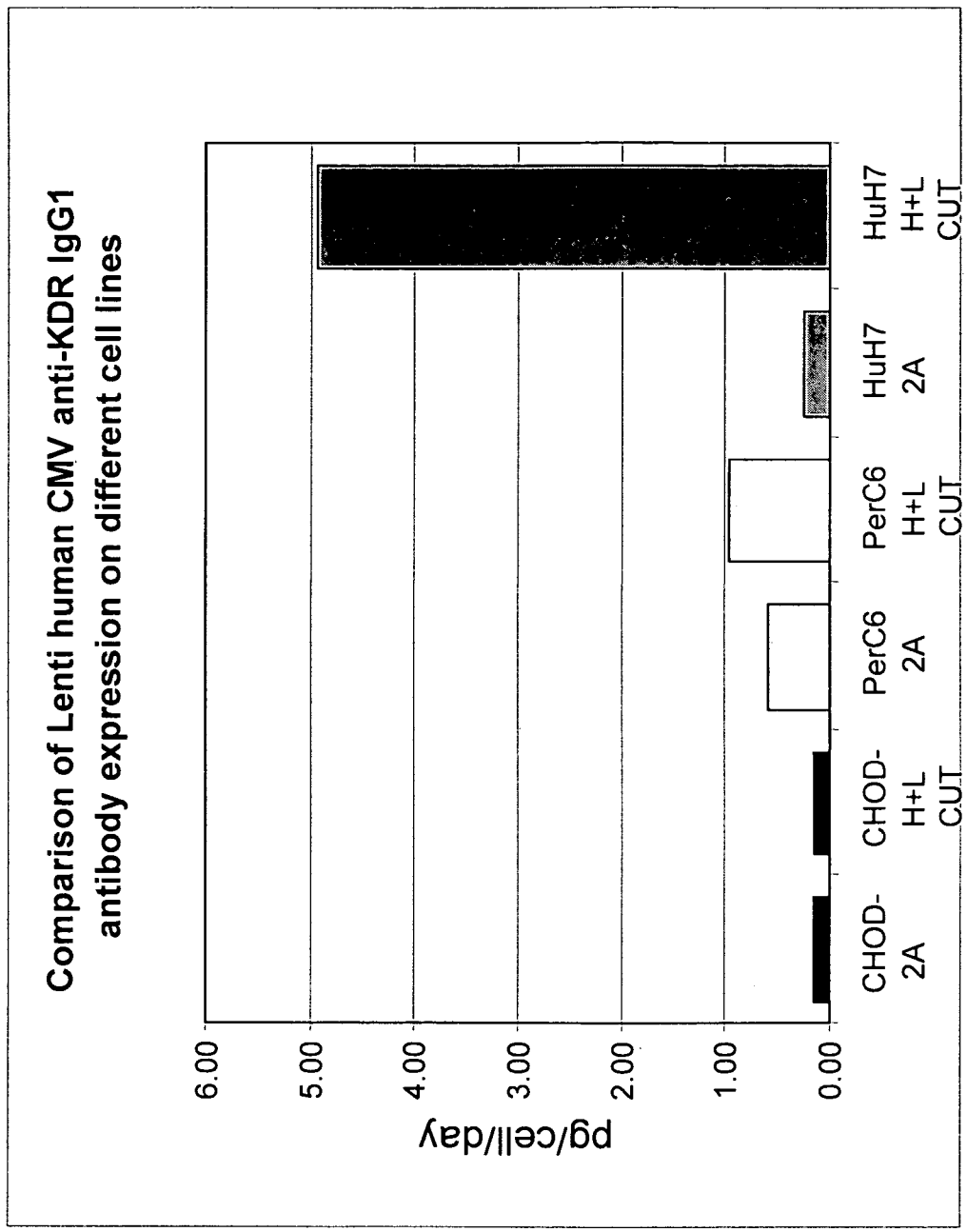
FIG. 7 illustrates the expression of a full length human CMV anti-KDR IgG1 monoclonal antibody in different cell lines (CHOD-, HuH7 and PerC6) following transduction with a lentivector, wherein 2A refers to expression of the heavy and light chain of KDR via a single vector including a self processing sequence.

FIG. 4 compares the antibody production from three cell lines (CHOD-, PerC6, HuH7) infected with lenti-2A-anti-DC101 FIG. 7 demonstrates that antibody is expressed in the same cell lines following infection with lenti-2A-anti-KDR using a CMV promoter.

Example 4

Alteration in the Amount of Lentivector and Changes in the Infection Intervals Can Increase Antibody Expression Levels and Decrease Time for Identifying Clones CHOD-cells were serially infected with lenti-2A-DC101 vector. Transductions done at one week intervals were compared with transduction is done at 2-3 day intervals. Infections were performed as described above. After each infection, the populations were saved, expanded, and assayed for antibody expression as described. Additionally, each cell population was analyzed for the number of lenti copies/cell by TaqMan PCR (Table 7).

TABLE 6

Comparison of antibody expression and lentivector copy number in CHOD-populations infected with Lenti-2A-DC101 at different time intervals

| | Experiment #1 | | | Experiment #2 | | |
|---|---|---|---|---|---|---|
| | Day of infection | Lenti copies/ cell | population pg/cell/day | Day of infection | Lenti copies/ cell | population pg/ cell/day |
| P2ng/ml | | | | | | |
| 50 | 1 | 7 | 1.60 | * | * | * |
| 100 | 1 | 37 | 2.26 | * | * | * |
| 200 (1x) | 1 | 20 | 3.62 | 1 | 20 | 4.58 |
| 200 (2x) | 8 | 40 | 7.07 | 3 | 41 | 7.62 |
| 200 (3x) | 15 | 36 | 7.50 | 5 | 58 | 8.05 |
| P24 ng/ml | | | | | | |
| 200 (4x) | 22 | 43 | 8.64 | 8 | 97 | 9.46 |
| 200 (5x) | 29 | 77 | 8.17 | 11 | 94 | 11.30 |
| 200 (6x) | * | * | * | 14 | 75 | 12.54 |
| 200 (7x) | * | * | * | 17 | 145 | 14.49 |
| 200 (8x) | * | * | * | 20 | 135 | 13.98 |
| 200 (9x) | * | * | * | 23 | 125 | 15.09 |

Taken together, the results suggest that successive transductions with lentivectors increases the number of antibody producer clones that generate high levels of antibodies. Integrated lentivector copies increase with each transduction and correlates with increasing antibody expression in the populations. It is interesting to note that decreasing the time between infections had a positive effect on antibody expression levels. Additionally, by decreasing the interval between infections from 1 week to 2-3 days, antibody expression was increased approximately 2-fold and the overall infection process was decreased by a week.

Example 8

Figure 8:
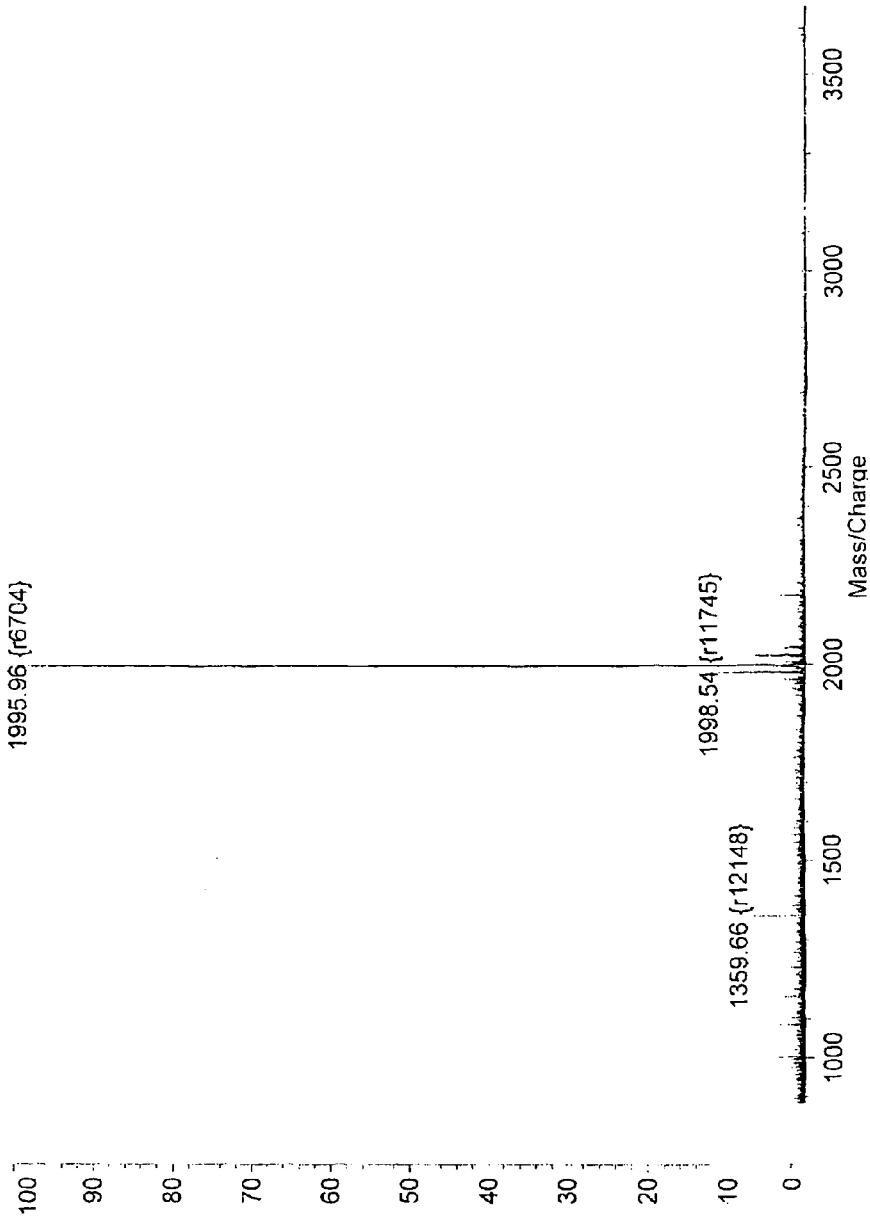
FIG. 8 illustrates the results of mass spectral analysis of purifies IgG protein produced following transfection of an HF2AL plasmid encoding into CHO cells, followed by furin cleavage and treatment with carboxypeptidase.

Removal of Extra Amino Acids Derived from Furin Cleavage Site at C-Terminus by Carboxypeptidases It has been shown that after furin cleavage newly exposed basic amino acids at the C-terminus of proteins can be removed by carboxypeptidases, we hypothesized that all additional amino acid derived from the furin cleavage site at the C-terminus of antibody heavy chain can be removed by using a furin cleavage site that consists of exclusively basic amino acids, i.e. R or K. In testing a number of furin cleavage sites with all basic amino acids, one construct was developed wherein the last amino acid K at the C-terminus of antibody heavy chain was deleted and the antibody heavy and light chains were linked with a furin cleavage site RKRR and a 2A sequence. The plasmid DNA was transfected into CHO cells in 10 cm tissue culture dish and the antibody protein was purified from the supernatant by protein A affinity chromatography. The purified IgG protein was separated in SDS-PAGE and the heavy chain band was sliced out from the gel. The heavy chain protein was then cleaved by Cyanogen Bromide (CNBr) and the resulting peptides were analyzed by mass spectrometer. Mass spectral analysis showed a strong peak that corresponds to the C-terminal fragment of the antibody heavy chain (FIG. 8). No peaks were observed in the spectrum that would represent the C-terminal fragment plus any amino acid(s) derived from the furin cleavage site. This data strongly suggested that the RKRR site facilitates efficient removal of extra amino acids at the C-terminus of the antibody heavy chain in HF2AL constructs, resulting in expression of the antibody heavy chain without any extra amino acid residues.

Example 9

Figure 9:
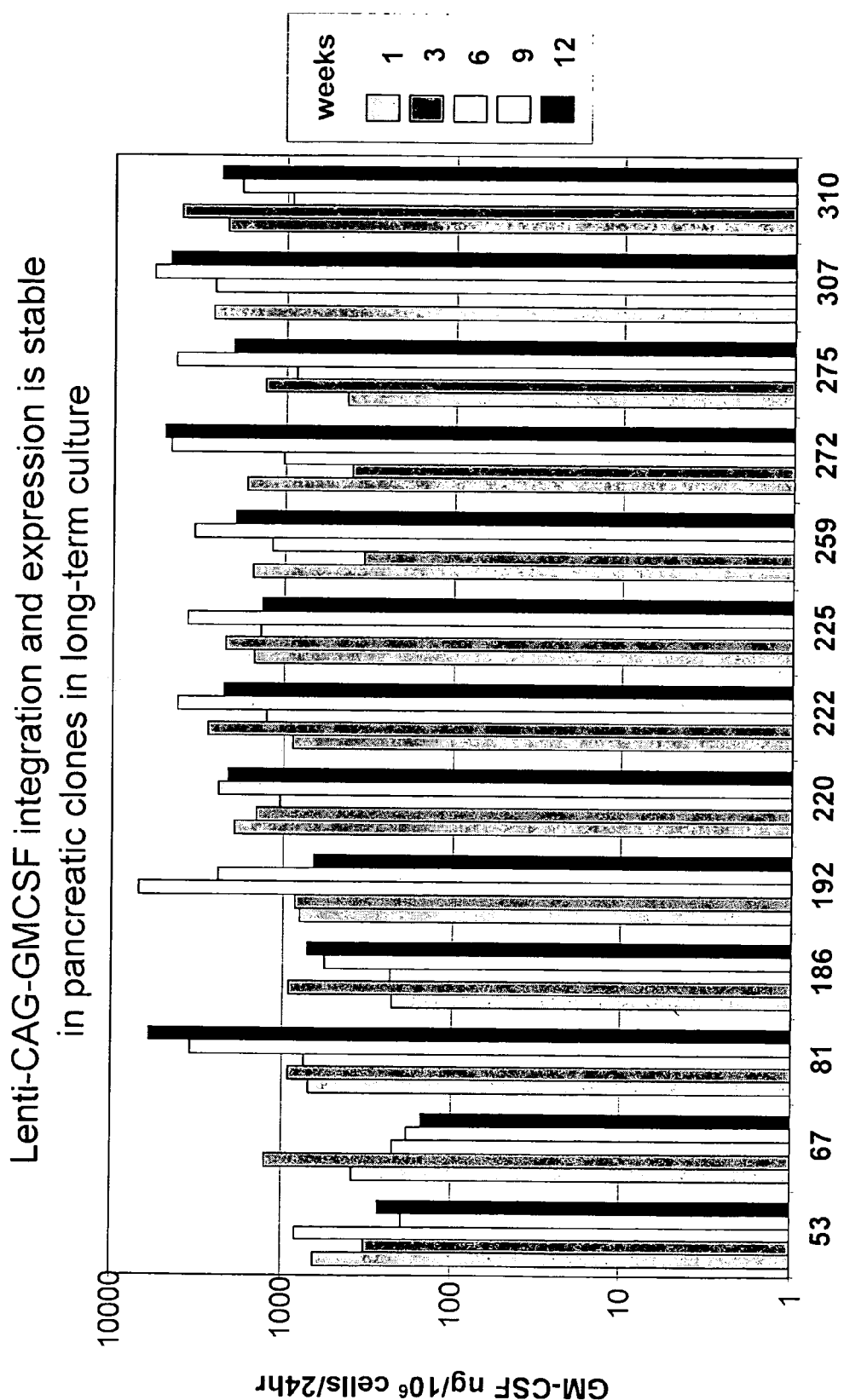
FIG. 9 demonstrates the results of a stability study of thirteen pancreatic clones transduced with a lentiviral vector encoding human GM-CSF. The GM-CSF expression level of clones expressing 500-2500 ng/$10^6$ cells/24 hr GM-CSF was maintained in continuous culture for 12 weeks with GM-CSF expression levels tested at 3-week intervals.

Stable Long-Term Expression of Lentivectors in Human Pancreatic and Mouse CT26 Cells Lentiviral vectors expressing human GMCSF from a CAG promoter were prepared by transient transfection, as described. Pancreatic cells were cultured and $3 \times 10^4$ cells were spinoculated with 1 ml of lentivirus and 8 ug/ml polybrene for 4 hrs at 3400 rpm, then plated in a 6 well plate with fresh medium. A total of three infections were performed at 2 week intervals. The populations from each infection were labeled "1x, 2x, and 3x." The 3x population was dilution cloned, and 1280 clones were picked and transferred to 96 well plates. Supernatants from these clones were screened for GM-CSF expression by ELISA. Nearly all clones were positive for human GM-CSF expression, and 88 clones were expanded to 6-well plates and re-assayed. Thirteen clones expressing 500-2500 ng/$10^6$ cells/24 hr GM-CSF were expanded to 10 cm plates, reassayed again, and put into a stability study. For the stability study the cells were maintained in continuous culture for 12 weeks with GM-CSF expression levels checked at 3 week intervals. FIG. 9 demonstrates that in 13 clones lentivector GM-CSF expression was stable for 12 weeks of continuous culture in medium that did not contain any selection.

Figure 10:
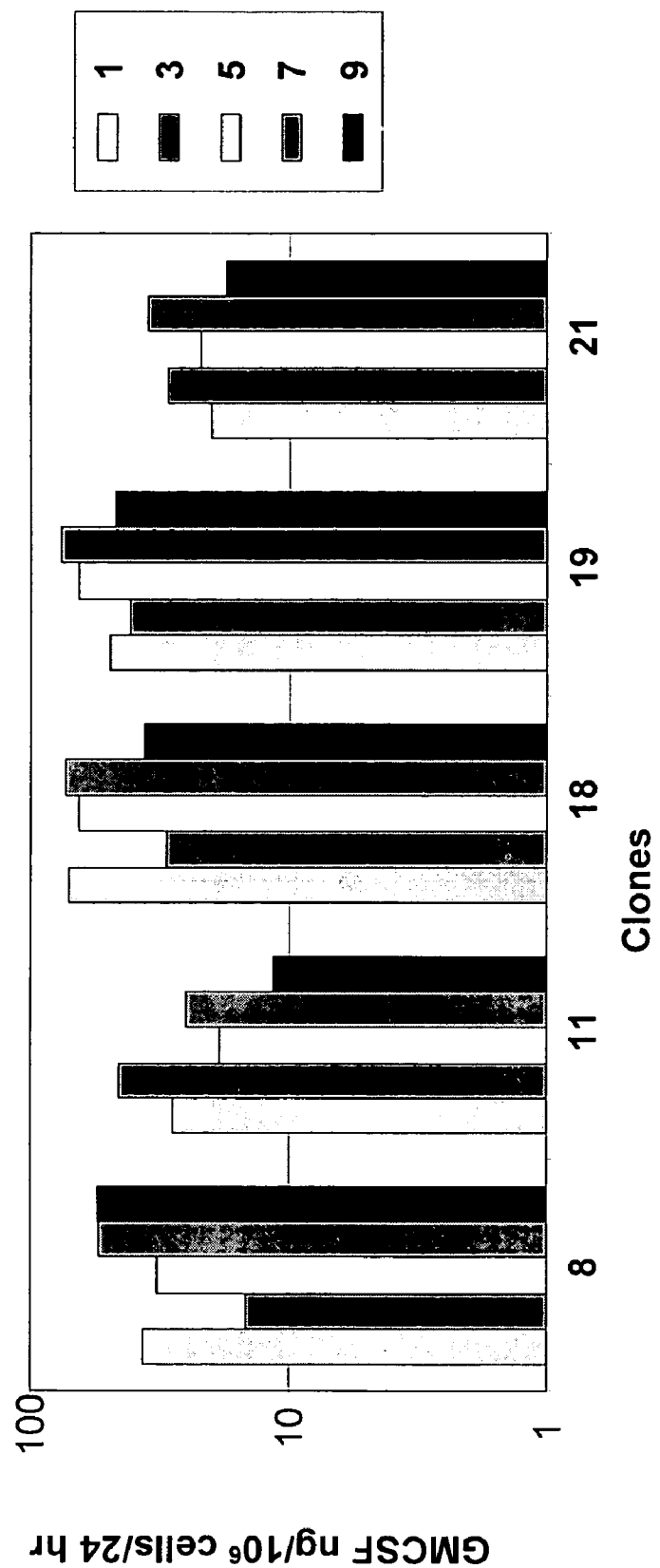
FIG. 10 demonstrates the results of a stability study of CT26 clones transduced with a lentiviral vector encoding murine GM-CSF, where the GM-CSF expression level of the CT26 rodent cell lines was shown to be stable for at least 9 weeks of continuous culture.

In a second lentivector expression stability study, long-term expression of mouse GM-CSF-producing clones was evaluated using CT26 cells (mouse adenocarcinoma cells) transduced with lentiviral vector expressing mouse GM-CSF. The CT26 cells were spinoculated and cloned as described. Five clones expressing GM-CSF were selected for a stability study. At weeks 1, 3, 5, 7 and 9, the cells were assayed for GM-CSF expression by ELISA. The results shown in FIG. 10 show that 5 clones exhibited stable GM-CSF expression over the course of the study.

Both the pancreatic and CT26 GM-CSF expression experiments demonstrate that lentivector generate clones are stable in long-term culture.

Example 10

Stable Long-Term Expression Of Lentivectors in CHO-S Cells

Lentiviral vectors expressing human DC101-IgG1 or KDR-IgG4 from a CAG promoter were prepared. The lentivector construct contained a 33 amino acid sequence from Foot and Mouth Disease Virus (FMDV) designated as 2A14 (SEQ ID NO:9) and an optimized furin sequence RKRR (SEQ ID NO:15), referred to herein as the "Lenti-DC101 vector". Suspension adapted, serum-free CHO-S cells or suspension adapted NSO cells—were transfected with the lentivector construct. The DC101 antibody coding sequence was modified so that the C terminal contains a methionine that can be cleaved for Mass Spec analysis.

CHO-S cells were serially infected with 200 ng P24 of the Lenti-DC101 vector at 2 to 3 day intervals. The populations were assayed for DC101 expression by ELISA (Table 1), and the data demonstrate that a steady increase in antibody production resulted following each infection, with no impact on the doubling times.

TABLE 7

DC101 Expression from CHO-S Cells Infected with Lenti-DC101-furin/2A14 by ELISA

| # of infections | Doubling time (hrs) | pg/cell/day |
|---|---|---|
| 1x | 18 | 7 |
| 2x | 18 | 9 |
| 3x | 19 | 19 |
| 4x | 19 | 18 |
| 5x | 17 | 16 |
| 6x | 18 | 22 |
| 7x | 19 | 24 |

Populations of cell that were infected 4× and 7×, respectively, were subcloned and analyzed for DC101 production. When compared, the clones derived from the population infected 7× generally had higher levels of DC101 expression than the clones from the population infected 4× (Table 2).

TABLE 8

DC101 expression by CHO-S cells infected 4x or 7x with Lenti-DC101-furin/2A14.

| Range of pg/ cell/day | 4x population | 7x population |
|---|---|---|
| 1 | 1 | 0 |
| 10 | 18 | 4 |
| 20 | 19 | 13 |
| 30 | 5 | 12 |
| 40 | 3 | 7 |
| 50 | 0 | 3 |
| 60 | 0 | 3 |
| 70 | 0 | 3 |
| 80 | 0 | 1 |
| 90 | 0 | 0 |
| 100 | 0 | 0 |
| 110 | 0 | 0 |
| 120 | 0 | 1 |
| Total Clones | 46 | 47 |

A panel of clones isolated from the 2×, 3× and 4× infected populations were subfected to continuous culture in 10 ml shaker flasks for 12 weeks and evaluated at one week intervals for stability of DC101 production. The clones were found to be stable (Table 3).

TABLE 9

Long Term DC101 expression by CHO-S cells infected with Lenti-DC101-furin/2A14.

Clones: pg/cell/day

| weeks | 4x-4 | 4x-3 | 4x-2 | 4x-1 | 3x-3 | 2x-8 | 2x-5 |
|---|---|---|---|---|---|---|---|
| 1 | 61.8 | 71.7 | 45.6 | 34.9 | 22.4 | 28.7 | 23.3 |
| 2 | 76.2 | 59.3 | 51.0 | 34.8 | 24.1 | 25.6 | 23.2 |
| 3 | 89.3 | 79.0 | 101.2 | 66.5 | 41.9 | 37.8 | 45.4 |
| 4 | 67.2 | 73.6 | 58.0 | 35.9 | 43.7 | 65.4 | 62.0 |
| 5 | 61.8 | 75.7 | 67.9 | 21.1 | 23.8 | 24.8 | 16.2 |
| 6 | 99.5 | 62.6 | 49.8 | 47.4 | 30.4 | 30.8 | 23.3 |
| 7 | 58.3 | 57.4 | 56.9 | 45.5 | 24.4 | 24.4 | 23.5 |
| 8 | 63.4 | 44.2 | 54.7 | 23.9 | 35.3 | 21.2 | 22.2 |
| 9 | 62.0 | 36.9 | 57.4 | 23.2 | 20.7 | 27.6 | 22.7 |
| 10 | 64.2 | 42.7 | 57.3 | 30.0 | 20.8 | 18.6 | 23.5 |
| 11 | 54.6 | 48.1 | 38.3 | 24.6 | 22.9 | 22.9 | 28.0 |
| 12 | 55.7 | 52.4 | 31.4 | 26.2 | 24.5 | 27.8 | 33.9 | the doubling times stabilized at less than 20 hours (Table 4).

TABLE 10

Doubling Time of DC101 expressing CHO-S cells infected with Lenti-DC101-furin/2A14.

Clones: Doubling time (hrs)

| weeks | 4x-4 | 4x-3 | 4x-2 | 4x-1 | 3x-3 | 2x-8 | 2x-5 |
|---|---|---|---|---|---|---|---|
| 1 | 17.1 | 25.5 | 16.2 | 15.5 | 16.6 | 16.2 | 14.0 |
| 2 | 21.2 | 30.1 | 17.7 | 16.7 | 17.1 | 16.7 | 16.2 |
| 3 | 21.2 | 35.7 | 21.2 | 21.2 | 18.1 | 18.1 | 18.7 |
| 4 | 21.2 | 29.1 | 21.2 | 16.2 | 22.4 | 29.4 | 22.9 |
| 5 | 17.1 | 19.4 | 16.2 | 15.5 | 16.4 | 15.9 | 15.2 |
| 6 | 18.1 | 19.4 | 15.8 | 16.2 | 15.9 | 15.9 | 14.9 |
| 7 | 20.2 | 19.4 | 16.6 | 18.1 | 16.2 | 15.5 | 14.9 |
| 8 | 17.2 | 18.1 | 16.6 | 15.9 | 17.8 | 15.2 | 15.9 |
| 9 | 18.1 | 17.2 | 17.1 | 16.2 | 16.4 | 15.2 | 15.5 |
| 10 | 16.6 | 17.1 | 17.2 | 14.9 | 16.0 | 15.1 | 15.3 |
| 11 | 19.7 | 16.6 | 16.2 | 15.7 | 15.6 | 15.5 | 15.9 |
| 12 | 19.1 | 18.1 | 15.9 | 16.2 | 16.2 | 15.9 | 14.7 |

Clones 4x-3 and 4x-4 were analyzed for genetic stability by Southern blot. DNA was extracted from both clones at weeks 1 and 7, digested with restriction enzymes EcoR I or Nsi I overnight, run on a 1% agarose/TBE gel and probed with a 592 bp fragment from the HC region. The standard is a serial dilution of EcoR I-digested DC101 plasmid in a background of 10 mg of genomic CHO-S DNA. The EcoR I releases a 2.2 kb fragment in both clones, and Clone 4x-4 appears to have several partial integrants. With both restriction enzymes the two clones have stable integration patterns from 1 to 7 weeks, demonstrating genetic stability.

Binding and neutralization assays were done to establish that antibodies from these clones were biologically equivalent to antibody produced from a hybridoma. In the binding assays 96-well plates were coated with recombinant Flk-1, incubated with serial dilutions of supernatants from clone 7x-24, the DC101 hybridoma, or a control, and quantified with anti-rat IgG1 HRP. The results show that the antibodies bind equivalently (Table 5).

TABLE 11

Binding of DC101 expressed from CHO-S cells infected with Lenti-DC101-furin/2A14 relative to DC101 Produced by a hybridoma.

| ng/ml | Mock | CHO-S | Hybridoma |
| --- | --- | --- | --- |
| 1000 | 0.152 | 1.144 | 1.121 |
| 333 | 0.149 | 0.993 | 0.894 |
| 111 | 0.152 | 0.616 | 0.724 |
| 37 | 0.121 | 0.486 | 0.585 |
| 12 | 0.120 | 0.412 | 0.403 |
| 4 | 0.104 | 0.274 | 0.312 |
| 0 | 0.118 | 0.129 | 0.117 |

A neutralization assay was carried out using supernatants from Clone 7x-24, a DC101 hybridoma and a negative control. Each supernatant was serially diluted and mixed with Flk-1, then incubated on 96-well plate pre-coated with human VEGF and read with anti-Flk-1-HRP. The antibodies generated from the 7x-24 clone neutralized the Flk-1 binding at a level equivalent to the hybridoma-produced DC 101 antibody (Table 6).

TABLE 12

Neutralization Assay of DC101 antibody produced by clone 7x-24 versus hybridoma-produced DC101.

| ng/ml | Mock | CHO-S | Hybridoma |
| --- | --- | --- | --- |
| 1000 | 1.278 | 0.184 | 0.193 |
| 333 | 1.28 | 0.237 | 0.357 |
| 111 | 1.203 | 0.43 | 0.635 |
| 37 | 1.195 | 0.826 | 0.834 |
| 12 | 1.134 | 0.945 | 0.931 |
| 4 | 1.152 | 1.043 | 0.992 |
| 0 | 1.089 | 1.069 | 1.105 |

The clones were tested for replication competent lentivirus by a TaqMan assay for VSV.G sequences. To establish the sensitivity of the assay, a cell line known to contain 1 copy of VSV-G envelope was spiked into a background of CHO cells ranging from 10-10,000 cells. DNA samples were prepared and assayed for the presence of VSV.G sequences. The sensitivity of this assay allows for detection of one VSV.G sequence in a background of 10,000 cells. The three clones and the CHO-S control cells were all negative for replication-competent lentiviral sequences.

TABLE 13

Sequences for Cell 164.1

| (SEQ ID) | SEQUENCE |
| --- | --- |
| NO: 1 | LLNFDLLKLAGDVESNPGP |
| NO: 2 | TLNFDLLKLAGDVESNPGP |
| NO: 3 | LLKLAGDVESNPGP |
| NO: 4 | NFDLLKLAGDVESNPGP |
| NO: 5 | QLLNFDLLKLAGDVESNPGP |
| NO: 6 | APVKQTLNFDLLKLAGDVESNPGP |
| NO: 7 | VTELLYRMKRAETYCPRPLLAIHPTEARHKQKIVAPVKQTLNFDLLKLAGDVESNPGP |
| NO: 8 | LLAIHPTEARHKQKIVAPVKQTLNFDLLKLAGDVESNPGP |
| NO: 9 | EARHKQKIVAPVKQTLNFDLLKLAGDVESNPGP |
| NO: 10 | Furin consensus sequence or site RXK(R)R |
| NO: 11 | Factor Xa cleavage sequence or site: IE(D)GR |
| NO: 12 | Signal peptidase I cleavage sequence or site: e.g., LAGFATVAQA |
| NO: 13 | Thrombin cleavage sequence or site: LVPRGS |
| NO: 14 | Furin site - RKKR |
| NO: 15 | Furin site-RKRR |
| NO: 16 | Furin site-RRKR |
| NO: 17 | Furin site - RRRR |

What is claimed is:

1. A method for producing a recombinant immunoglobulin or a recombinant immunoglobulin fragment, comprising the steps of:
   a) transducing a host cell with a lentivector, said lentivector comprising: in the 5' to 3' direction, a promoter operably linked to an open reading frame transcriptional unit comprising (1) a sequence encoding a heavy chain of an immunoglobulin or a fragment of the heavy chain, (2) a sequence encoding a furin cleavage site, (3) a sequence encoding a 2A self-processing cleavage site, wherein the 2A self-processing cleavage site is the FMDV 2A oligopeptide SEQ ID NO: 9, and (4) a sequence encoding a light chain of an immunoglobulin or a fragment of the light chain;
   b) expressing the recombinant immunoglobulin or the recombinant immunoglobulin fragment in said transduced host cell, wherein said sequence encoding the heavy chain of the immunoglobulin or the fragment of the heavy chain and said sequence encoding the light chain of the immunoglobulin or the fragment of the light chain are expressed from the same host cell.

2. The method according to claim 1, wherein the furin cleavage site has the consensus sequence of SEQ ID NO: 15.

3. The method according to claim 1, wherein said promoter is a cytomegalovirus enhancer/chicken beta-actin promoter (CAG).

4. The method according to claim 2, further comprising the step of treating the expressed recombinant immunoglobulin or the recombinant immunoglobulin fragment with a carboxypeptidase.

5. The method according to claim 1, wherein said host cell is a CHO cell.

6. A method for producing a recombinant immunoglobulin or a recombinant immunoglobulin fragment in vitro, comprising the steps of:
   a) transducing a host cell with a first lentivector comprising a promoter operably linked to a sequence encoding a heavy chain of an immunoglobulin or a fragment of the heavy chain, wherein said host cell produces a first lentivirus comprising the promoter operably linked to the sequence encoding the heavy chain of the immunoglobulin or the fragment of the heavy chain;
   b) transducing a host cell or clones from the host cell used in step (a) with a second lentivector comprising a promoter operably linked to a sequence encoding a light chain of an immunoglobulin or a fragment of the light chain, wherein said host cell produces a second lentivirus comprising the promoter operably linked to the sequence encoding the light chain of the immunoglobulin or the fragment of the light chain;
   c) infecting and reinfecting a producer cell multiple times with a plurality of the first lentivirus and a plurality of the second lentivirus wherein the producer cell is selected from the group consisting of CHO and CHOD-cells; and
   d) expressing the recombinant immunoglobulin or the recombinant immunoglobulin fragment in said producer cell.

7. The method according to claim 6, wherein each of said first and second lentivectors comprises a cytomegalovirus enhancer/chicken beta-actin promoter (CAG).

8. The method according to claim 6 wherein said host cell and the clones from the host cell are Chinese hamster ovary (CHO) cells.

9. The method according to claim 6, wherein said recombinant immunoglobulin or recombinant immunoglobulin fragment is expressed for at least 3 months at a level greater than 20 pg/cell/day.

10. A method of producing a recombinant immunoglobulin or a recombinant immunoglobulin fragment comprising infecting a producer cell at least four times with a recombinant lentivirus comprising in the 5' to 3' direction, a promoter operably linked to an open reading frame transcriptional unit comprising (1) a sequence encoding a heavy chain of an immunoglobulin or a fragment of the heavy chain, (2) a sequence encoding a furin cleavage site, (3) a sequence encoding a 2A self-processing cleavage site, wherein the 2A self-processing cleavage site is the FMDV 2A oligopeptide SEQ ID NO: 9, and (4) a sequence encoding a light chain of an immunoglobulin or a fragment of the light chain, wherein said recombinant immunoglobulin or the recombinant immunoglobulin fragment is expressed at a level greater than 20 pg/cell/day.

11. The method of claim 1 wherein the recombinant immunoglobulin or the recombinant immunoglobulin fragment is expressed at a level greater than 20 pg/cell/day for at least three months.

12. The method according to claim 10, wherein the furin cleavage site has the consensus sequence SEQ ID NO: 15.

13. The method according to claim 10, wherein said promoter is a cytomegalovirus enhancer/chicken beta-actin promoter (CAG).

14. The method according to claim 12, further comprising the step of treating the expressed recombinant immunoglobulin or the recombinant immunoglobulin fragment with a carboxypeptidase.

15. The method according to claim 10, wherein said producer cell is selected from the group consisting of CHO and CHOD-cells.

16. The method according to claim 8 wherein the Chinese hamster ovary cells are CHOD-cells.

* * * * *